(12) United States Patent
Kawata et al.

(10) Patent No.: US 8,829,201 B2
(45) Date of Patent: Sep. 9, 2014

(54) ELECTROLYTE FORMULATIONS

(75) Inventors: Kentaro Kawata, Kanagawa Pref. (JP);
Hiroki Yoshizaki, Tokyo (JP); Hiromi Shinohara, Kanagawa Pref. (JP); Peer Kirsch, Seeheim-Jugenheim (DE); Nikolai (Mykola) Ignatyev, Duisburg (DE); William-Robert Pitner, Büttelborn (DE); Marlies Waterman, legal representative, Büttelborn (DE); Emil Ferdinand Aust, Mainz (DE)

(73) Assignee: Merck Patent GmbH, Darmstadt (DE)

( * ) Notice: Subject to any disclaimer, the term of this patent is extended or adjusted under 35 U.S.C. 154(b) by 242 days.

(21) Appl. No.: 13/542,903

(22) Filed: Jul. 6, 2012

(65) Prior Publication Data

US 2012/0318360 A1 Dec. 20, 2012

Related U.S. Application Data

(63) Continuation-in-part of application No. PCT/EP2011/000088, filed on Jan. 12, 2011.

(30) Foreign Application Priority Data

Jan. 18, 2010 (EP) .................................. 10000391

(51) Int. Cl.
| | | |
|---|---|---|
| C07D 295/037 | (2006.01) | |
| C07D 233/54 | (2006.01) | |
| C07F 5/02 | (2006.01) | |
| H01G 9/02 | (2006.01) | |
| H01G 9/20 | (2006.01) | |
| C07D 233/58 | (2006.01) | |
| H01M 10/0565 | (2010.01) | |
| H01M 10/0564 | (2010.01) | |
| H01M 10/0525 | (2010.01) | |

(52) U.S. Cl.
CPC ............... *C07F 5/022* (2013.01); *Y02E 10/52* (2013.01); *Y02E 60/12* (2013.01); *H01G 9/2013* (2013.01); *H01M 2300/0065* (2013.01); *C07D 295/037* (2013.01); *H01M 10/0525* (2013.01); *H01M 2300/0025* (2013.01); *C07D 233/58* (2013.01); *Y02E 10/542* (2013.01); *H01G 9/2059* (2013.01); *H01M 2300/0091* (2013.01); *H01M 10/0565* (2013.01); *H01G 9/2031* (2013.01); *H01M 10/0564* (2013.01)
USPC ........ 548/335.1; 548/579; 558/384; 252/62.2

(58) Field of Classification Search
USPC ................ 548/335.1, 579; 558/384; 252/62.2
See application file for complete search history.

(56) References Cited

U.S. PATENT DOCUMENTS

| | | | |
|---|---|---|---|
| 2006/0222584 A1* | 10/2006 | Welz-Biermann et al. | ... 423/377 |
| 2010/0229950 A1 | 9/2010 | Kuang | |
| 2011/0012048 A1 | 1/2011 | Zhang | |

FOREIGN PATENT DOCUMENTS

JP 2004-175666 A 6/2004

OTHER PUBLICATIONS

Wang et al. ("Enhance the Performance of Dye-sensitized Solar Cell by Co-grafting Amphiphilic Sensitizer and Hexadecylmalonic Acid on TiO2 Nanocrystals"; J. Phys. Chem. (B 2003), 107, 14336-14341).
Gorlov et al. ("Ionic Liquid Electrolytes for Dye-sensitized Solar Cells"; Dalton Trans. (2008), 2655-2666).
Barbe et al. ("Nanocrystalline Titanium Oxide Electrodes for Photovoltaic Applications"; J. Am. Ceram. Soc. (1997), 80(12), 3157-3171).

* cited by examiner

*Primary Examiner* — Joseph Kosack
(74) *Attorney, Agent, or Firm* — Rick Matos; Innovar, L.L.C.

(57) ABSTRACT

The present invention relates to electrolyte formulations comprising at least one imidazolium difluorodicyanoborate or pyrrolidinium difluorodicyanoborate and their use in an electrochemical and/or optoelectronic device such as a photovoltaic cell, a light emitting device, an electrochromic or photoelectrochromic device, an electrochemical sensor and/or biosensor, preferably their use in a dye or quantum dot-sensitized solar cell.

52 Claims, 5 Drawing Sheets

Tetracyanoborate

ELECTROLYTE FORMULATIONS

CROSS-REFERENCE TO EARLIER FILED APPLICATIONS

The present application claims the benefit of and is a continuation-in-part of international application No. PCT/EP2011/000088, filed Jan. 12, 2011, which claims the benefit of European Application EP 10000391.2, filed Jan. 18, 2010, the entire disclosures of which are hereby incorporated by reference.

FIELD OF THE INVENTION

The present invention relates to electrolyte formulations comprising at least one imidazolium difluorodicyanoborate or at least one pyrrolidinium difluorodicyanoborate and their use in an electrochemical and/or optoelectronic device such as a photovoltaic cell, a light emitting device, an electrochromic or photo-electrochromic device, an electrochemical sensor and/or biosensor, preferably their use in a dye-sensitized solar cell or quantum dot-sensitized solar cell.

BACKGROUND OF THE INVENTION

Electrolyte formulations form a crucial part of electrochemical and/or optoelectronic devices, and the performance of the device largely depends on the physical and chemical properties of the various components of these electrolytes.

Factors which are still impeding the technical application of many electrochemical and/or optoelectronic devices and in particular of dye or quantum dot-sensitized solar cells, concern lack of reliability caused by the volatility of organic solvents based electrolytes. It is very difficult to maintain a tight seal and retain the electrolyte in e.g. a DSC (dye-sensitized solar cell) panel, which has to withstand the temperature differences of daily day-night cycles and the concomitant thermal expansion of the electrolyte. This problem can be solved in principle by the use of ionic liquid-based electrolytes. For review "Ionic liquid electrolytes for dye-sensitized solar cells" see: M. Gorlov and L. Kloo, *Dalton Trans.*, 2008, p. 2655-2666.

Ionic liquids or liquid salts are typically ionic species which consist of an organic cation and a generally inorganic anion usually having melting points below 373 K. Various binary ionic liquid electrolytes have recently been applied to dye-sensitized solar cells. WO 2007/093961 and WO 2009/083901 describe, thus far, the best power conversion efficiencies obtained with ionic liquid-based electrolytes for DSC containing a significant quantity of organic salts with tetracyanoborate (TCB, [(NC)$_4$B]$^-$) anions.

However, there continues to be a demand for new and improved electrolytes based on ionic liquids with equal or improved DSC efficiency especially at a temperature below room temperature and well above the temperature at which liquid freezing and precipitation may take place (i.e. in the range of 0° C. to 20° C.).

Some of the compounds of Formula (I), below, with imidazolium cations are disclosed in WO 2004/072089; however, the publication does not describe an electrolyte formulation comprising compounds of Formula (I) as described herein, and it does not disclose the specific utility of these compounds as components of an electrolyte formulation for the given electrochemical and/or optoelectronic devices, especially for DSC.

Organic salts are described in JP2004-175666 which includes "onium" salts with anions of formula [(CN)$_a$X$_{4-a}$B]$^-$ in which X is a halogen atom and a is an integer of 1 to 3. Trifluorocyanoborate is disclosed as a preferred anion. Electrolyte formulations containing 1-ethyl-3-methylimidazolium trifluorocyanoborate, tetraethylammonium trifluorocyanoborate or trimethyl-propylammonium trifluorocyanoborate are disclosed. There is no suggestion that compounds of Formula (I) as described below would show such improved properties over compounds containing the trifluorocyanoborate anion and the same cation.

SUMMARY OF THE INVENTION

The object of the invention is therefore to provide improved electrolyte formulations for use in electrochemical and/or optoelectronic devices to provide increased power conversion efficiency; e.g. for use in a photovoltaic cell, a light emitting device, an electrochromic or photo-electrochromic device, an electrochemical sensor and/or biosensor. The electrolyte formulation is especially useful in dye-sensitized or quantum dot-sensitized solar cells, especially preferably for dye-sensitized solar cells over a broad temperature range, particularly additionally at low temperature. Low temperature is defined as the temperature range between −20° C. and 20° C. Surprisingly, it has been found that electrolyte formulations comprising difluorodicyanoborate anions fulfill such demands.

The present invention is a selection invention. Comparison data establishing the unexpectedly improved performance provided by the selected group of compounds described herein over compounds of the prior art are included herein. Without being held to a particular mechanism, it is believed that formulations comprising difluorodicyanoborate anions reduce the Nernst diffusion resistance of redox-couple species (e.g. I$^-$ and I$_3$$^-$) and charge transfer resistance at the counter electrode at low temperatures as defined above.

In some embodiments, the invention provides an electrolyte formulation comprising at least one compound of Formula (I)

$$Kt^+[B(CN)_2F_2]^- \quad (I)$$

wherein Kt$^+$ is an organic cation selected from the group of

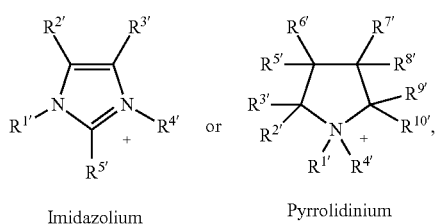

Imidazolium    Pyrrolidinium and
the substituents R$^{1'}$ to R$^{10'}$ each, independently of one another, denote: H, provided that that R$^{1'}$ and R$^{4'}$ are not both simultaneously H, meaning at least one is not H; straight-chain or branched alkyl having 1 to 20 C atoms, which optionally may be fluorinated; straight-chain or branched alkenyl having 2 to 20 C atoms and one or more double bonds, which optionally may be fluorinated; straight-chain or branched alkynyl having 2 to 20 C atoms and one or more triple bonds which optionally may be fluorinated; or straight-chain or branched alkoxyalkyl having 2 to 8 C atoms.

In some embodiments, the invention provides an electrolyte formulation comprising at least one compound (one or more compounds) of Formula (I) as described herein wherein $Kt^+$ of the compound of Formula (I) is

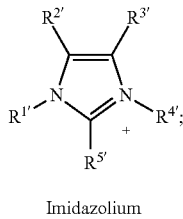

Imidazolium $R^{2'}$ and $R^{3'}$ are H;
$R^{5'}$ is H or straight-chain or branched alkyl having 1 to 4 C atoms; and
$R^{1'}$ and $R^{4'}$ are each independently upon each occurrence a straight chain or branched alkyl having 1-20 C atoms, or a straight-chain or branched alkenyl having 3 C atoms.

In some embodiments, the invention provides an electrolyte formulation comprising at least one compound (one or more compounds) of Formula (I) as described herein wherein $Kt^+$ of the compound of Formula (I) is

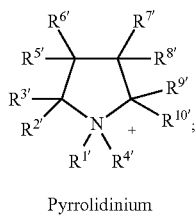

Pyrrolidinium $R^{2'}$, $R^{3'}$, $R^{5'}$ to $R^{10'}$ are H; and
$R^{1'}$ and $R^{4'}$ are each independently of one another (independently selected upon each occurrence) a straight chain or branched alkyl having 1-20 C atoms.

Particularly preferably, the electrolyte formulation according to the invention comprises at least one compound of Formula (I) with the given formula for imidazolium and the definitions of the substituents $R^{1'}$ to $R^{5'}$ or the particularly preferred definitions or examples of dialkylimidazolium or 1-alkoxyalkyl-3-alkylimidazolium as described herein.

In some embodiments wherein $Kt^+$ is pyrrolidinium: a) $R^{1'}$ and $R^{4'}$ are alkyl, wherein $R^{1'}$ and $R^{4'}$ can be the same or different upon each occurrence; and $R^{2'}$, $R^{3'}$ and $R^{5'}$ to $R^{10'}$ are hydrogen; b) $R^{1'}$ and $R^{4'}$ are $C_1$-$C_{10}$-alkyl, wherein $R^{1'}$ and $R^{4'}$ can be the same or different upon each occurrence; and $R^{2'}$, $R^{3'}$ and $R^{5'}$ to $R^{10'}$ are hydrogen; c) $R^{1'}$ is alkyl; $R^{4'}$ is alkoxyalkyl; and $R^{2'}$, $R^{3'}$ and $R^{5'}$ to $R^{10'}$ are hydrogen; d) $R^{1'}$ is $C_1$-$C_{10}$-alkyl; $R^{4'}$ is $C_1$-$C_{10}$-alkoxy-$C_1$-$C_{10}$-alkyl; and $R^{2'}$, $R^{3'}$ and $R^{5'}$ to $R^{10'}$ are hydrogen; or e) $R^{1'}$ is $C_1$-$C_4$-alkyl; $R^{4'}$ is $C_1$-$C_3$-alkoxy-$C_1$-$C_3$-alkyl; and $R^{2'}$, $R^{3'}$ and $R^{5'}$ to $R^{10'}$ are hydrogen.

In some embodiments wherein $Kt^+$ is pyrrolidinium: $R^{1'}$ is selected from the group consisting of alkyl, $C_1$-$C_{10}$-alkyl, $C_1$-$C_4$-alkyl, methyl, ethyl, propyl, butyl, pentyl, hexyl, heptyl, octyl, nonyl and decyl; $R^{4'}$ is selected from the group consisting of alkyl, $C_1$-$C_{10}$-alkyl, $C_1$-$C_{10}$-alkoxy-$C_1$-$C_{10}$-alkyl, $C_1$-$C_3$-alkoxy-$C_1$-$C_3$-alkyl, methyl, ethyl, propyl, butyl, pentyl, hexyl, heptyl, octyl, nonyl, decyl, methoxymethyl, methoxyethyl, ethoxyethyl, and ethoxymethyl; and $R^{2'}$, $R^{3'}$ and $R^{5'}$ to $R^{10'}$ are hydrogen; wherein $R^{1'}$ and $R^{4'}$ are independently selected upon each occurrence.

In some embodiments wherein $Kt^+$ is pyrrolidinium: $R^{1'}$ is selected from the group consisting of methyl, ethyl, propyl butyl, pentyl, hexyl, heptyl, octyl, nonyl and decyl; $R^{4'}$ is selected from the group consisting of methyl, ethyl, propyl, butyl, pentyl, hexyl, heptyl, octyl, nonyl, decyl, methoxymethyl, methoxyethyl, ethoxyethyl, and ethoxymethyl; and $R^{2'}$, $R^{3'}$ and $R^{5'}$ to $R^{10'}$ are hydrogen; wherein $R^{1'}$ and $R^{4'}$ are independently selected upon each occurrence.

In some embodiments wherein $Kt^+$ is imidazolium: a) $R^{1'}$ and $R^{4'}$ are alkyl, wherein $R^{1'}$ and $R^{4'}$ can be the same or different upon each occurrence; and $R^{2'}$, $R^{3'}$ and $R^{5'}$ are hydrogen; b) $R^{1'}$, $R^{5'}$ and $R^{4'}$ are alkyl, wherein $R^{1'}$, $R^{5'}$ and $R^{4'}$ can be the same or different upon each occurrence; and $R^{3'}$ and $R^{2'}$ are hydrogen; c) $R^{1'}$ and $R^{4'}$ are $C_1$-$C_{10}$-alkyl, wherein $R^{1'}$ and $R^{4'}$ can be the same or different upon each occurrence; and $R^{2'}$, $R^{3'}$ and $R^{5'}$ are hydrogen; d) $R^{1'}$, $R^{5'}$ and $R^{4'}$ are $C_1$-$C_{10}$-alkyl, wherein $R^{1'}$, $R^{5'}$ and $R^{4'}$ can be the same or different upon each occurrence; and $R^{3'}$ and $R^{2'}$ are hydrogen; e) $R^{1'}$, $R^{5'}$ and $R^{4'}$ are $C_1$-$C_3$-alkyl, wherein $R^{1'}$, $R^{5'}$ and $R^{4'}$ can be the same or different upon each occurrence; and $R^{3'}$ and $R^{2'}$ are hydrogen; f) $R^{1'}$ and $R^{4'}$ are $C_1$-$C_{10}$-alkyl, wherein $R^{3'}$ and $R^{4'}$ can be the same or different upon each occurrence; $R^{5'}$ is H or $C_1$-$C_{10}$-alkyl or $C_1$-$C_{10}$-alkoxy-$C_1$-$C_{10}$-alkyl; and $R^{3'}$ and $R^{2'}$ are hydrogen; g) $R^{1'}$ and $R^{4'}$ are $C_1$-$C_3$-alkyl, wherein $R^{1'}$ and $R^{4'}$ can be the same or different upon each occurrence; $R^{5'}$ is H or $C_1$-$C_3$-alkyl; and $R^{3'}$ and $R^{2'}$ are hydrogen; h) $R^{1'}$ is alkyl; $R^{4'}$ is alkoxyalkyl; and $R^{2'}$, $R^{3'}$ and $R^{5'}$ are hydrogen; i) $R^{1'}$ is alkyl; $R^{4'}$ is alkoxyalkyl; $R^{5'}$ is H or alkyl; and $R^{3'}$ and $R^{2'}$ are hydrogen; j) $R^{1'}$ is $C_1$-$C_{10}$-alkyl; $R^{4'}$ is $C_1$-$C_{10}$-alkoxy-$C_1$-$C_{10}$-alkyl; $R^{5'}$ is H or $C_1$-$C_{10}$-alkyl; and $R^{3'}$ and $R^{2'}$ are hydrogen; k) $R^{1'}$ is $C_1$-$C_{10}$-alkyl; $R^{4'}$ is $C_1$-$C_{10}$-alkoxy-$C_1$-$C_{10}$-alkyl; $R^{5'}$ is H or $C_1$-$C_{10}$-alkyl; and $R^{3'}$ and $R^{2'}$ are hydrogen; or l) $R^{1'}$ is $C_1$-$C_4$-alkyl or $C_1$-$C_2$-alkyl; $R^{4'}$ is $C_1$-$C_3$-alkoxy-$C_1$-$C_3$-alkyl; $R^{5'}$ is H or $C_1$-$C_3$-alkyl; and $R^{3'}$ and $R^{2'}$ are hydrogen.

In some embodiments wherein $Kt^+$ is imidazolium: $R^{1'}$ is selected from the group consisting of alkyl, $C_1$-$C_{10}$-alkyl, $C_1$-$C_4$-alkyl, methyl, ethyl, propyl, butyl, pentyl, hexyl, heptyl, octyl, nonyl and decyl; $R^{4'}$ is selected from the group consisting of alkyl, $C_1$-$C_{10}$-alkyl, $C_1$-$C_{10}$-alkoxy-$C_1$-$C_{10}$-alkyl, $C_1$-$C_3$-alkoxy-$C_1$-$C_3$-alkyl, methyl, ethyl, propyl, butyl, pentyl, hexyl, heptyl, octyl, nonyl, decyl, methoxymethyl, methoxyethyl, ethoxyethyl, and ethoxymethyl; $R^{5'}$ is hydrogen, methyl, ethyl, isopropyl, propyl or n-butyl or methoxymethyl, methoxyethyl, ethoxyethyl, and ethoxymethyl; and $R^{3'}$ and $R^{2'}$ are hydrogen; wherein each substituent is independently selected upon each occurrence.

In some embodiments wherein $Kt^+$ is imidazolium: $R^{1'}$ is selected from the group consisting of methyl, ethyl, propyl butyl, pentyl, hexyl, heptyl, octyl, nonyl and decyl; $R^{4'}$ is selected from the group consisting of methyl, ethyl, propyl, butyl, pentyl, hexyl, heptyl, octyl, nonyl, decyl, methoxymethyl, methoxyethyl, ethoxyethyl, and ethoxymethyl; $R^{5'}$ is hydrogen, methyl, ethyl, isopropyl, propyl or n-butyl; and $R^{3'}$ and $R^{2'}$ are hydrogen; wherein each substituent is independently selected upon each occurrence.

Some embodiments of the invention include those wherein: a) the electrolyte formulation comprises the compound of Formula (I); b) the electrolyte formulation further comprises one or more of the necessary or optional constituents described herein; c) the electrolyte formulation further comprises one or more further salts; d) the electrolyte formulation further comprises one or more solvents; e) the electrolyte formulation further comprises iodine; f) the electrolyte formulation further comprises one or more iodide salts; g) the electrolyte formulation is a binary system comprising a compound of Formula (I) and a further salt; h) the electrolyte formulation is a ternary system comprising a compound of Formula (I) and two further salts; i) the electrolyte formulation further comprises one or more compounds containing a nitrogen atom having non-shared electron pairs; j) the electrolyte formulation further comprises one or more redox active species; k) the electrolyte formulation further comprises one or more polymers; l) the electrolyte formulation further comprises one or more metal oxide nanoparticles; m) the electrolyte formulation further comprises one or more dyes; n) the electrolyte formulation comprises one or more compounds of the Formula (I) and one or more constituents selected from the group consisting of: one or more further salts, one or more solvents, iodine, one or more iodide salts, one or more compounds containing a nitrogen atom having non-shared electron pairs, one or more redox active species, one or more polymers, one or more metal oxide nanoparticles, one or more dyes, guanidinium salts such as thiocyanate salts or iodide salts and a combination thereof; and/or o) the electrolyte formulation comprises less than 50% wt, less than 40% wt, less than 30% wt, less than 20% wt, less than 10% wt, less than 5% wt, or less than 1% wt of organic solvent or the electrolyte formulation excludes an organic solvent.

Some embodiments of the invention include those wherein: a) at least one compound of Formula (I) is prepared prior to its inclusion in the electrolyte formulation; b) at least one compound of Formula (I) is formed in situ in the electrolyte formulation; and/or c) at least one compound of Formula (I) is prepared by mixing a composition comprising a compound of Formula (II) with a composition comprising a compound of Formula (III), wherein the compound of Formula (II) is defined as follows:

$$\text{Cat}^+[B(CN)_2F_2]^- \tag{II}$$

wherein Cat$^+$ is an inorganic cation or an organic cation selected from the group consisting of guanidinium, tetramethylammonium and triethyloxonium;
and the compound of Formula (III) is defined as follows:

$$\text{Kt}^+[\text{An}]^- \tag{III},$$

wherein [An]$^-$ is an inorganic or organic anion; and
Kt$^+$ is an organic cation selected from the group of

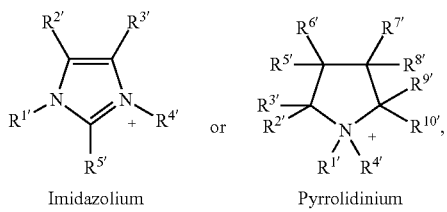

Imidazolium          Pyrrolidinium and
the substituents $R^{1'}$ to $R^{10'}$ are each, independently of one another, defined as described herein, whereby one or more compounds of Formula (I) are formed.

Some embodiments of the invention include those wherein the electrolyte formulation comprises one or more compounds of the Formula (I) and one or more constituents selected from the group consisting of: one or more further salts, one or more solvents, iodine, one or more iodide salts, one or more compounds containing a nitrogen atom having non-shared electron pairs, one or more redox active species, one or more polymers, one or more metal oxide nanoparticles, one or more dyes, guanidinium thiocyanate and a combination thereof.

In some embodiments, the mixing is done with heating or with one or more of the compositions having been heated. In some embodiments, the electrolyte formulation is mixed to a homogeneous solution.

Some embodiments of the invention include those wherein: a) Cat$^+$ is an inorganic cation selected from the group consisting of lithium-, sodium-, potassium-, rubidium-, silver-, magnesium-, calcium- or zinc-cations; and/or b) [An]$^-$ is an anion selected from the group consisting of halide, iodide, chloride, bromide, fluoride, polyhalide, thiocyanate, fluoroalkanesulfonate, fluoroalkanecarboxylate, nitrate, tetrafluoroborate, hexafluorophosphate, dicyanamide, tricyanomethide, alkylsulfonate, triflate and alkylsulfate, wherein the alkyl group is an alkyl group having 1 to 4 C atoms or a fluoroalkane chain having 1 to 4 C atoms, preferably perfluorinated fluoroalkyl having 1 to 4 C atoms. Fluoroalkane-chain or fluoroalkyl is preferably perfluorinated.

The electrolyte formulation of the invention may be used or included in an optoelectronic and/or electrochemical device such as a photovoltaic cell, a light emitting device, an electrochromic device, a photo-electrochromic device, an electrochemical sensor, a biosensor, a double layer capacitor or an electrochemical battery, for example in a lithium ion battery. The invention therefore provides one or more optoelectronic or electrochemical devices comprising the electrolyte formulation as described herein.

In some embodiments, the invention provides an electrochemical and/or optoelectronic device, which is a photovoltaic cell, a light emitting device, an electrochromic or photo-electrochromic device, an electrochemical sensor and/or biosensor, comprising an electrolyte formulation comprising at least one compound of Formula (I)

$$\text{Kt}^+[B(CN)_2F_2]^- \tag{I}$$

wherein Kt$^+$ is an organic cation selected from the group of

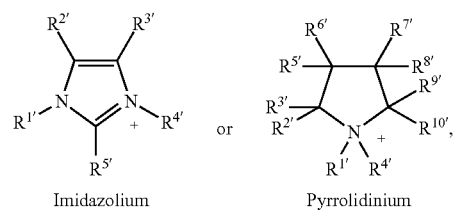

Imidazolium          Pyrrolidinium wherein the substituents $R^{1'}$ to $R^{10'}$ each, independently of one another, denote:
H, provided that $R^{1'}$ and $R^{4'}$ are not both simultaneously H;
straight-chain or branched alkyl having 1-20 C atoms, which optionally may be fluorinated; straight-chain or branched alkenyl having 2-20 C atoms and one or more double bonds, which optionally may be fluorinated; straight-chain or branched alkynyl having 2-20 C atoms and one or more triple bonds which optionally may be fluorinated; or straight-chain or branched alkoxyalkyl having 2 to 8 C atoms.

In some embodiments of the invention, the device is a dye-sensitized solar cell or a quantum dot-sensitized solar cell. In a particular embodiment, the device is a dye-sensitized solar cell.

The invention also includes embodiments wherein the term "comprises" is construed to mean "includes", "contains" "comprises", "consists essentially of" or "consists of". The invention includes all combinations of the aspects, embodiments and sub-embodiments of the invention disclosed herein.

DETAILED DESCRIPTION OF THE FIGURES

The following figures form part of the present description and describe exemplary embodiments of the claimed invention. The skilled artisan will, in light of these figures and the description herein, be, able to practice the invention without undue experimentation.

DETAILED DESCRIPTION OF THE INVENTION

Figure 1:
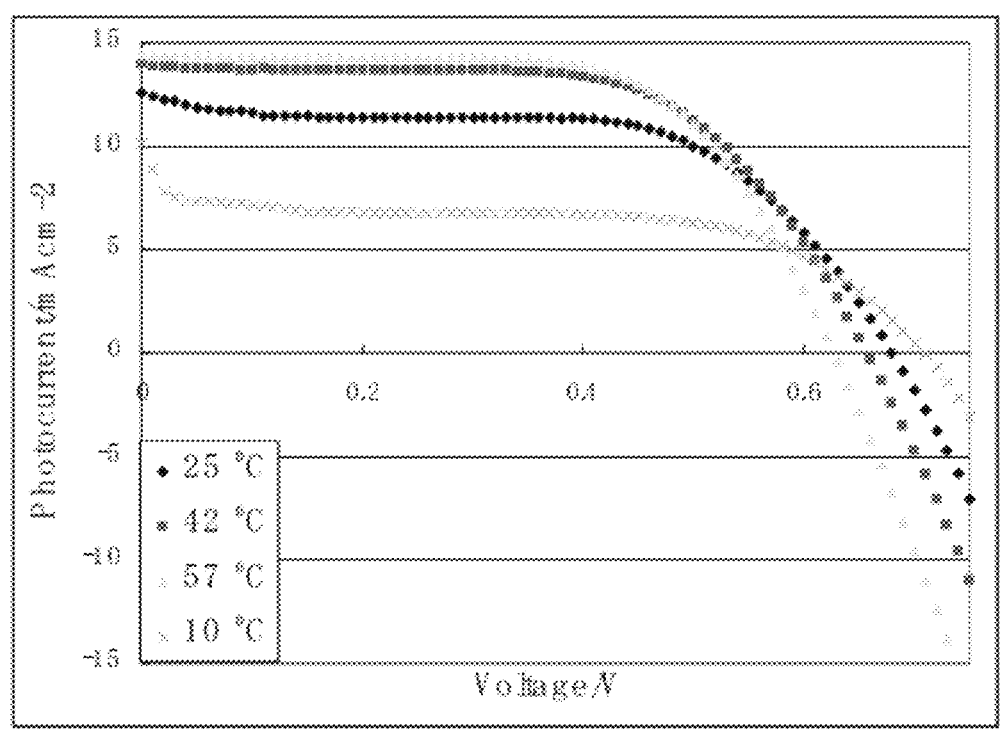
FIG. 1 depicts the photocurrent density-voltage curves for device A containing the electrolyte formulation A which curves form the basis for table 2 at 10° C., 25° C., 42° C. and 57° C.

The invention provides an electrolyte formulation comprising a compound of the Formula (I). The invention also provides an optoeletronic and/or electrochemical device comprising an electrolyte formulation comprising a compound of the Formula (I).

The term electrolytes is used herein in the sense of electrolyte formulation as described herein and will be used equally to refer to the electrolyte formulation.

The term "fluorinated" means that at least one H atom of a particular group being referred to is substituted by an F atom. As used herein, the phrase "optionally may be fluorinated", means the group being referred to optionally comprises at least one —F atom or plural —F atoms, i.e. partially fluorinated or perfluorinated.

A straight-chain or branched alkyl having 1-20 C atoms denotes an alkyl group having 1, 2, 3, 4, 5, 6, 7, 8, 9, 10, 11, 12, 13, 14, 15, 16, 17, 18, 19 or 20 C (carbon) atoms, for example methyl, ethyl, isopropyl, n-propyl, isobutyl, n-butyl, ten-butyl, n-pentyl, 1-methylbutyl, 2-methylbutyl, 3-methylbutyl, 1,1-dimethylpropyl, 1,2-dimethylpropyl, 2,2-dimethylpropyl, 1-ethylpropyl, n-hexyl, n-heptyl, n-octyl, ethylhexyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl or eicosyl. An alkyl group may be optionally and independently fluorinated.

A straight-chain or branched alkenyl group, in which one or more, or a plurality of, double bonds are present, comprises 2 to 20 C atoms and can be selected from the group consisting of, for example, —$C_2H_3$ to —$C_{20}H_{39}$, —$C_2H_3$ to —$C_{10}H_{19}$, —$C_2H_3$ to —$C_9H_{17}$, —$C_9H_{17}$, —$C_{10}H_{19}$ to —$C_{20}H_{39}$, allyl, 2-butenyl, 3-butenyl, iso-butenyl, sec-butenyl, 4-pentenyl, iso-pentenyl, hexenyl, heptenyl, and octenyl. In some embodiments, alkenyl is selected from the group consisting of allyl, 2-butenyl, 3-butenyl, iso-butenyl, sec-butenyl, 4-pentenyl, iso-pentenyl or hexenyl. An alkenyl group may be optionally and independently fluorinated.

A straight-chain or branched alkynyl, in which one or more, or a plurality of, triple bonds are present, comprises having 2 to 20 C atoms and can be selected from the group consisting of, for example, —$C_2H_1$ to —$C_{20}H_{37}$, —$C_2H_1$ to —$C_{10}H_{17}$, —$C_2H_1$ to —$C_1H_{15}$, —$C_9H_{15}$, —$C_{10}H_{17}$ to —$C_{20}H_{37}$, ethynyl, 1-propynyl, 2-propynyl, 2-butynyl, 3-butynyl, 4-pentynyl, 3-pentynyl, hexynyl, heptynyl, and octynyl. In some embodiments, alkynyl is selected from the group consisting of ethynyl, 1-propynyl, 2-propynyl, 2-butynyl, 3-butynyl, 4-pentynyl, 3-pentynyl and hexynyl. An alkynyl group may be optionally and independently fluorinated.

A straight-chain or branched alkoxyalkyl comprising 2 to 12 C atoms and an oxygen atom along the backbone, can be selected from the group consisting of, for example, $C_1$-$C_{11}$-alkoxy-$C_1$-$C_{11}$-alkyl, $C_1$-$C_5$-alkoxy-$C_1$-$C_7$-alkyl, methoxymethyl, 1-methoxyethyl, 1-methoxypropyl, 1-methoxy-2-methyl-ethyl, 2-methoxy-propyl, 2-methoxy-2-methyl-propyl, 1-methoxybutyl, 1-methoxy-2,2-dimethyl-ethyl, 1-methoxy-pentyl, 1-methoxyhexyl, 1-methoxy-heptyl, ethoxymethyl, 1-ethoxyethyl, 1-ethoxypropyl, 1-ethoxy-2-methyl-ethyl, 1-ethoxybutyl, 1-ethoxy-2,2-dimethyl-ethyl, 1-ethoxypentyl, 1-ethoxyhexyl, 1-ethoxyheptyl, propoxymethyl, 1-propoxyethyl, 1-propoxypropyl, 1-propoxy-2-methyl-ethyl, 1-propoxybutyl, 1-propoxy-2,2-dimethyl-ethyl, 1-propoxypentyl, butoxymethyl, 1-butoxyethyl, 1-butoxypropyl or 1-butoxybutyl. In some embodiments, an alkoxyalkyl group is selected from the group consisting of $C_1$-alkoxy-$C_1$-$C_4$-alkyl, methoxymethyl, 1-methoxyethyl, 2-methoxy-propyl, 1-methoxypropyl, 2-methoxy-2-methyl-propyl and 1-methoxybutyl.

In some embodiments, suitable substituents $R^{1'}$ to $R^{10'}$ of compounds of the Formula (I), besides H, can be preferably: $C_1$-$C_{20}$-alkyl or, in particular $C_1$-$C_6$-alkyl groups. The substituents $R^{1'}$ to $R^{10'}$ can be independently selected upon each occurrence.

In some embodiments, the substituents $R^{1'}$ and $R^{4'}$ are each, independently of one another, preferably selected from the group consisting of $C_1$-$C_6$-alkyl, methyl, ethyl, isopropyl, propyl, butyl, sec-butyl, tert-butyl, n-pentyl and n-hexyl. In some embodiments, they are preferably selected from the group consisting of methyl, ethyl, n-butyl or n-hexyl. In some embodiments, the two substituents $R^{1'}$ and $R^{4'}$ are preferably different. In other embodiments, the substituents $R^{1'}$ and $R^{4'}$ are the same.

The substituents $R^{2'}$, $R^{3'}$ and $R^{5'}$ to $R^{10'}$ can be, independently of one another, selected from the group consisting of H, $C_1$-$C_4$-alkyl, methyl, ethyl, isopropyl, propyl, butyl, sec-butyl and tert-butyl. The substituents $R^{2'}$, $R^{3'}$ and $R^{5'}$ to $R^{10'}$ can be the same or different. Two or more of the substituents $R^{2'}$, $R^{3'}$ and $R^{5'}$ to $R^{10'}$ can be the same or different.

In some embodiments, when $Kt^+$ is an imidazolium ring, $R^{5'}$ is particularly preferably selected from the group consisting of H, methyl, ethyl, isopropyl, propyl and n-butyl, or from the group consisting of H and methyl.

In some embodiments, when $Kt^+$ is an imidazolium ring, $R^{2'}$ and $R^{3'}$ are preferably H.

In some embodiments, when $Kt^+$ is an pyrrolidinium ring, the substituents $R^{2'}$, $R^{3'}$, $R^{5'}$ to $R^{10'}$ are preferably H.

Preferred 1,1-dialkylpyrrolidinium cations are, for example, 1,1-dimethyl-pyrrolidinium, 1-methyl-1-ethylpyrrolidinium, 1-methyl-1-propylpyrrolidinium, 1-methyl-1-butylpyrrolidinium, 1-methyl-1-pentylpyrrolidinium, 1-methyl-1-hexylpyrrolidinium, 1-methyl-1-heptylpyrrolidinium, 1-methyl-1-octylpyrrolidinium, 1-methyl-1-nonyl-pyrrolidinium, 1-methyl-1-decylpyrrolidinium, 1,1-diethylpyrrolidinium, 1-ethyl-1-propyl-pyrrolidinium, 1-ethyl-1-butylpyrrolidinium, 1-ethyl-1-pentylpyrrolidinium, 1-ethyl-1-hexylpyrrolidinium, 1-ethyl-1-heptylpyrrolidinium, 1-ethyl-1-octylpyrrolidinium, 1-ethyl-1-nonylpyrrolidinium, 1-ethyl-1-decylpyrrolidinium, 1,1-dipropylpyrrolidinium, 1-propyl-1-methylpyrrolidinium, 1-propyl-1-butylpyrrolidinium, 1-propyl-1-pentylpyrrolidinium, 1-propyl-1-hexylpyrrolidinium, 1-propyl-1-heptylpyrrolidinium, 1-propyl-1-octyl-pyrrolidinium, 1-propyl-1-nonylpyrrolidinium, 1-propyl-1-decylpyrrolidinium, 1,1-dibutyl-pyrrolidinium, 1-butyl-1-pentylpyrrolidinium, 1-butyl-1-hexylpyrrolidinium, 1-butyl-1-heptylpyrrolidinium, 1-butyl-1-octylpyrrolidinium, 1-butyl-1-nonylpyrrolidinium, 1-butyl-1-decylpyrrolidinium, 1,1-dipentylpyrrolidinium, 1-pentyl-1-hexylpyrrolidinium, 1-pentyl-1-heptylpyrrolidinium, 1-pentyl-1-octylpyrrolidinium, 1-pentyl-1-nonylpyrrolidinium, 1-pentyl-1-decylpyrrolidinium, 1,1-dihexylpyrrolidinium, 1-hexyl-1-heptylpyrrolidinium, 1-hexyl-1-octylpyrrolidinium, 1-hexyl-1-nonylpyrrolidinium, 1-hexyl-1-decylpyrrolidinium, 1,1-dihexylpyrrolidinium, 1-hexyl-1-heptylpyrrolidinium, 1-hexyl-1-octylpyrrolidinium, 1-hexyl-1-nonylpyrrolidinium, 1-hexyl-1-decylpyrrolidinium, 1,1-diheptyl-pyrrolidinium, 1-heptyl-1-octylpyrrolidinium, 1-heptyl-1-nonylpyrrolidinium, 1-heptyl-1-decylpyrrolidinium, 1,1-dioctylpyrrolidinium, 1-octyl-1-nonylpyrrolidinium, 1-octyl-1-decylpyrrolidinium, 1,1-dinonylpyrrolidinium, 1-nonyl-1-decylpyrrolidinium or 1,1-didecylpyrrolidinium. Very particular preference is given to 1-butyl-1-methyl-pyrrolidinium or 1-propyl-1-methylpyrrolidinium.

Preferred 1-alkyl-1-alkoxyalkylpyrrolidinium cations are, for example, 1-methoxymethyl-1-methyl-pyrrolidinium, 1-methoxymethyl-1-ethyl-pyrrolidinium, 1-(2-methoxyethyl)-1-methylpyrrolidinium, 1-(2-methoxyethyl)-1-ethylpyrrolidinium, 1-(2-methoxyethyl)-1-propylpyrrolidinium, 1-(2-methoxyethyl)-1-butylpyrrolidinium, 1-(2-ethoxyethyl)-1-methylpyrrolidinium, 1-ethoxymethyl-1-ethyl-pyrrolidinium, 1-ethoxymethyl-1-methylpyrrolidinium. Very particular preference is given to 1-(2-methoxyethyl)-1-methylpyrrolidinium.

Preferred 1,3-dialkylimidazolium cations are, for example, 1-ethyl-3-methylimidazolium, 1-methyl-3-propylimidazolium, 1,2,3-trimethylimidazolium, 1-ethyl-2,3-dimethylimidazolium, 1-propyl-2,3-dimethylimidazolium, 1-butyl-2,3-dimethylimidazolium, 1-butyl-3-methylimidazolium, 1-methyl-3-pentylimidazolium, 1-ethyl-3-propylimidazolium, 1-butyl-3-ethylimidazolium, 1-ethyl-3-pentylimidazolium, 1-butyl-3-propylimidazolium, 1,3-dimethylimidazolium, 1,3-diethylimidazolium, 1,3-dipropylimidazolium, 1,3-dibutylimidazolium, 1,3-dipentylimidazolium, 1,3-dihexylimidazolium, 1,3-diheptylimidazolium, 1,3-dioctylimidazolium, 1,3-dinonylimidazolium, 1,3-didecylimidazolium, 1-hexyl-3-methylimidazolium, 1-heptyl-3-methylimidazolium, 1-methyl-3-octylimidazolium, 1-methyl-3-nonylimidazolium, 1-decyl-3-methylimidazolium, 1-ethyl-3-hexylimidazolium, 1-ethyl-3-heptylimidazolium, 1-ethyl-3-octylimidazolium, 1-ethyl-3-nonylimidazolium or 1-decyl-3-ethylimidazolium. Particularly preferred cations are 1-ethyl-3-methylimidazolium, 1-butyl-3-methylimidazolium or 1-methyl-3-propylimidazolium.

Preferred 1-alkoxyalkyl-3-alkylimidazolium cations are, for example 1-methoxymethyl-3-methylimidazolium, 1-methoxymethyl-3-ethylimidazolium, 1-methoxymethyl-3-butylimidazolium, 1-(2-methoxyethyl)-3-methylimidazolium, methoxyethyl)-3-ethylimidazolium, 1-(2-methoxyethyl)-3-propylimidazolium, 1-(2-methoxyethyl)-3-butylimidazolium, 1-(2-ethoxyethyl)-3-methylimidazolium, 1-ethoxymethyl-3-methylimidazolium.

Preferred 1-alkenyl-3-alkylimidazolium cations are, for example 1-allyl-3-methyl-imidazolium or 1-allyl-2,3-dimethylimidazolium.

Kt⁺ compounds of the invention are readily commercially available. Otherwise, they can be prepared according to U.S. Pat. No. 7,292,289, the disclosure of which is hereby incorporated. A Kt compound having a tertiary nitrogen is mixed and alkylated with an alkyl halide or a dialkyl sulfate or alkylsulfonate, optionally with heating, to form the Kt⁺ salt having a quaternary nitrogen and a halide or sulfate or sulfonate, respectively, counterion. The reaction may require heating and pressure, such as in an autoclave, when using an alkylating compound of low reactivity, such as an alkoxyethyl halide or alkoxymethyl halide.

In chemistry, an electrolyte is any substance containing free ions that make the substance electrically conductive. The most typical electrolyte is an ionic solution, but molten electrolytes and solid or polymeric electrolytes are also possible.

An electrolyte formulation according to the invention is therefore an electrically conductive medium, due to the presence of at least one substance that is present in a dissolved and/or in molten state and dissociates into ionic species, i.e. supporting an electric conductivity via motion of ionic species.

Particularly preferably, the electrolyte formulation according to the invention comprise at least one compound of Formula (I) with the given formula for imidazolium as described or preferably described herein.

An electrolyte formulation of the invention can be prepared simply by mixing two or more of the ingredients. The electrolyte formulation is preferably a homogenous mixture. Alternatively, the electrolyte formulation can be prepared by heating and mixing the ingredients. Alternatively, the electrolyte formulation can be prepared by mixing the ingredients, wherein one or more of the ingredients is heated before mixing. A combination of processes can be used.

The compound of Formula (I) included in the electrolyte formulation can be prepared first and then added to or mixed with other components of the formulation. The compound of Formula (I) can be prepared as described herein or in U.S. Pat. No. 7,292,289 or U.S. Pat. No. 7,645,434, the entire disclosures of which are hereby incorporated by reference.

Alternatively, the compound of Formula (I) included in the electrolyte formulation can be formed in situ by mixing a compound of Formula (II) with a compound of Formula (III), whereby a compound of Formula (I) is formed. In situ preparation of the compound of Formula (I) can be performed by mixing a compound of Formula (II) with a compound of Formula (III) in the presence or absence of one or more other constituents of an electrolyte formulation, whereby a compound of Formula (I) is formed. In some embodiments, in situ formation requires heating one or more ingredients before, during and/or after mixing.

In some embodiments, a compound of Formula (I) is prepared by mixing a difluorocyanoborate salt $(Cat[BF_2(CN)_2])$ with an imidazolium salt or pyrrolidinium salt $(Kt[An])$, optionally with heating and optionally in the presence of one or more other constituents and optionally in the presence of an alkaline material, whereby a compound of Formula (I) $(Kt[BF_2(CN)_2])$ and a by-product salt $Cat[An]$ (comprising the respective counterions of the starting material salts) are formed as follows.

$$Kt[An]+Cat[BF_2(CN)_2] \rightarrow Kt[BF_2(CN)_2]+Cat[An]$$

Typical molar concentrations of the difluorodicyanoborate anion in the electrolyte formulations range from 0.1 to 4 M, preferably from 0.8 to 3.5 M. This molar concentration in the electrolyte may be achieved with one or more compounds of Formula (I) or with mixtures comprising at least one compound of Formula (I) and at least one inorganic salt or a further organic salt with the difluorodicyanoborate anion. In some embodiments, the further organic salt comprises an organic cation similar to the organic cation of the compound of Formula (I) and difluorodicyanoborate as anion. In some embodiments, the difluorodicyanoborate anion in the electrolyte formulation is present in molar excess over the organic cation of the compound of Formula (I). In some embodiments, part of the difluorodicyanoborate anion present in the electrolyte formulation is complexed with an inorganic cation, i.e. part of the DDB is present as an inorganic cation salt. In some embodiments, the inorganic cation salt of DDB, when present, comprises less than 40% wt, less than 30% wt, less than 20% wt, less than 10% wt or less than 5% wt of the electrolyte formulation. In some embodiments, the electrolyte formulation comprises N-butylpyridinium DDB and at least one compound of the Formula (I), whereby the total molar concentration of DDB present in the electrolyte formulation is as defined herein. In some embodiments, the electrolyte formulation comprises at least one compound of the Formula (I), whereby the total molar concentration of (amount of) DDB present in the electrolyte formulation is as defined herein.

Inorganic salts with difluorodicyanoborate anions are for example lithium difluorodicyanoborate, sodium difluorodicyanoborate, potassium difluorodicyanoborate, rubidium difluorodicyanoborate, silver difluorodicyanoborate, magnesium di(difluorodicyanoborate), calcium di(difluorodicyanoborate) or zinc di(difluorodicyanoborate).

Preferably, the target or required molar concentration of DDB can be achieved with at least one compound of Formula (I) as described or preferably described herein.

For the purpose of the present invention, the molar concentration of DDB refers to the concentration at 25° C.

Other components of the electrolyte formulation are one or several further salts, solvents, iodine and others, as indicated further herein.

If the electrolyte formulation is a binary system, it comprises two salts, one further salt or iodide salt and a compound of Formula (I) as described herein. If the electrolyte formulation is a ternary system, it comprises two further salts and/or iodide salts and a compound of Formula (I) as described herein. The binary system comprises 90-10 weight %, preferably 7040 weight %, more preferably 55-40 weight of the further salt or iodide salt and 10-90 weight %, preferably 30-70 weight % or more preferably 45-60 weight % of the compound of formula I as described herein. The percentages in this paragraph are expressed with respect to the total weight of salts (=100 weight %) present in the electrolyte formulation according to the invention. Amounts of further, generally optional components (additives) indicated herein, such as N-containing compounds having unshared electron pairs, iodine, solvents, polymers, and nanoparticles, for example, are not considered in determining this particular weight percentage. The same percentages apply to ternary or quaternary systems which means the total of the further salts has to be used in the given ranges, e.g. two further ionic liquids are comprised in e.g. 90-10 weight. % in the electrolyte formulation according to the invention.

In some embodiments, a binary formulation comprises 10-90 weight % of compound of Formula I and 90-10 weight % of further salt. In some embodiments, a ternary formulation comprises: a) 10-90 weight % of compound of Formula I and 90-10% weight % total, independently of each other, of two different further salts. The weight percentages expressed in this paragraph are based upon the total weight of all salts of the compound of formula I and all further salts present in the formulation. In some embodiments, the compound of formula I and further salt or all further salts comprise 30-70% weight of the electrolyte formulation. In addition, the electrolyte formulation can comprise iodide salt as part of the redox-couple with iodine.

In each occurrence, the cation is independently selected from the cations broadly or specifically disclosed herein. The cation of the compound of Formula I can be the same as or different than the cation of the further salt or of the iodide salt.

In some embodiments, the electrolyte formulation excludes an organic solvent when one or more compounds of the Formula (I) is a liquid at the operating temperature or under the conditions of use of the electrolyte formulation. In some embodiments, the electrolyte formulation comprises one or more compounds of the Formula (I), one or more redox couples (such as the couple of iodine and an iodide salt), optionally one or more further salts, and optionally one or more constituents (additives).

According to another embodiment of the present invention, the electrolyte formulation comprises at least one "further salt" comprising an organic cation and an anion, wherein the organic cation comprises a quaternary nitrogen or sulfonium cation, and the anion is selected from the group consisting of Cl⁻, Br⁻, a polyhalide ion, a fluoroalkanesulfonate, a fluoroalkanecarboxylate, a tris(fluoroalkylsulfonyl)methide, a bis(fluoroalkylsulfonyl)imide, a nitrate, a hexafluorophosphate, a tris-, bis- or mono-(fluoroalkyl)fluorophosphate, a tetrafluoroborate, a dicyanamide, a tricyanomethide, a tetracyanoborate, a thiocyanate, an alkylsulfonate or an alkylsulfate, with fluoroalkane chain having 1 to 20 C atoms, preferably perfluorinated, fluoroalkyl having 1 to 20 C atoms and alkyl having 1 to 20 C atoms. Fluoroalkane-chain or fluoroalkyl is preferably perfluorinated.

Preferably, the anion of the further salt is selected from the group consisting of thiocyanate or tetracyanoborate, wherein a particularly preferred anion is tetracyanoborate ($[(NC)_4B]^-$).

The cation of the at least one further salt or of a preferred further salt may be selected amongst organic cations as defined herein for the compounds of Formula I including also the preferred definitions. Exemplary cations include compounds comprising a quaternary nitrogen atom, preferably cyclic organic cations such as pyridinium, imidazolium, triazolium, pyrrolidinium or morpholinium or sulfonium cation such as triethylsulfonium.

However, to limit the amount of different cations in the electrolyte formulations, especially for DSC, the organic cation of the further salt and/or iodide salt may be selected from the definitions for the cations of the compounds of Formula (I). Therefore, according to another preferred embodiment of the present invention, the electrolyte formulation comprises at least one compound of Formula (I) as described above and at least one iodide salt in which the organic cations are independently selected from the group of

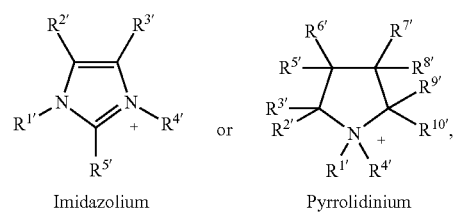

Imidazolium      Pyrrolidinium in which the substituents $R^{1'}$ to $R^{10'}$ have a meaning as described or preferably described above.

In another embodiment of the invention, guanidinium thiocyanate may be added to the electrolyte formulation according to the invention.

The present invention relates furthermore to an electrolyte formulation comprising at least one compound of formula I as described above or preferably described together with redox active species (redox couple) such as iodide/tri-iodide, Ferrocene derivatives or Co(II)/Co(III) complex couples such as Co(II)/Co(III)(dbbip)$_2$ in which dbbip means 2,6-bis(1'-butylbenzimidazol-2'-yl)pyridine, Co(II)/Co(III)(bpy)$_3$ where bpy denotes bipyridine or alkylated bipyridine derivates thereof, the counter anion being either perchlorate, fluoroperfluoroalkylphosphate such as perfluoroethylpentafluorophosphate, or (fluoro)cyanoborate, particularly tetracyanoborate, or preferably together with an iodide/triodide redox couple comprising iodine and at least one iodide salt.

The electrolyte formulation of the invention preferably comprises iodine ($I_2$). Preferably, it comprises from 0.0005 to 7 mol/dm$^3$, more preferably 0.01 to 5 mol/dm$^3$ and most preferably from 0.05 to 1 mol/dm$^3$ of $I_2$.

The iodide salt consists of an inorganic or organic cation and r as anion. There exists no limitation as to the structure, kind or type of cation. However, to limit the amount of different cations in the electrolyte formulations, especially for DSC, the organic cation of the iodide salt is preferably as described herein for the compounds of Formula (I). In some particularly preferred embodiments, the electrolyte formulation comprises at least one iodide salt wherein the organic cation is independently selected from the group of

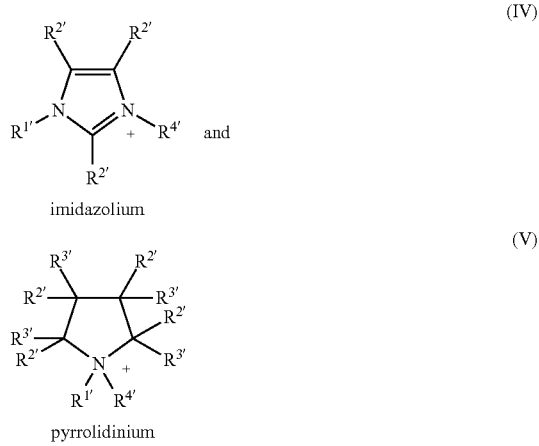

wherein:
$R^{2'}$ and $R^{3'}$ each, independently of one another, denote H or straight-chain or branched alkyl having 1 to 20 C atoms;
$R^{1'}$ and $R^{4'}$ are each, independently of one another, selected from the group consisting of:
straight-chain or branched alkyl having 1-20 C atoms, which optionally may be partially fluorinated,
straight-chain or branched alkenyl having 2-20 C atoms and one or more double bonds, which optionally may be partially fluorinated,
straight-chain or branched alkynyl having 2-20 C atoms and one or more triple bonds, which optionally may be partially fluorinated.

Some embodiments of the invention include those wherein, the organic cation of the iodide salt is: a) the same as the cation Kt$^+$ of at least one compound of Formula (I) in the electrolyte formulation; b) selected from Kt$^+$ as defined herein for at least one compound of Formula (I) in the electrolyte formulation; c) an imidazolium cation of Formula (IV), wherein $R^{1'}$, $R^{2'}$ and $R^{4'}$ are as defined herein; d) an imidazolium cation of Formula (IV), wherein: 1) $R^{1'}$ is alkyl, allyl or alkenyl; $R^{4'}$ is alkyl, allyl or alkenyl; and $R^{2'}$ is hydrogen or alkyl; or 2) $R^{1'}$ is alkyl, allyl or alkenyl; $R^{4'}$ is alkyl; and $R^{2'}$ is hydrogen; or 3) $R^{1'}$ is $C_1$-$C_6$-alkyl or allyl; $R^{4'}$ is $C_1$-$C_2$-alkyl; and $R^{2'}$ is hydrogen; or 4) $R^{1'}$ is methyl, ethyl, propyl, butyl, pentyl, hexyl, or allyl; $R^{4'}$ is methyl; and $R^{2'}$ is hydrogen; e) a pyrrolidinium cation of Formula (V), wherein $R^{1'}$ to $R^{4'}$ are as defined herein; f) a pyrrolidinium cation of Formula (V), wherein: 1) $R^{1'}$ is alkyl, allyl or alkenyl; $R^{4'}$ is alkyl, allyl or alkenyl; and $R^{2'}$ and $R^{3'}$ are hydrogen or alkyl; or 2) $R^{1'}$ is alkyl; $R^{4'}$ is alkyl; and $R^{2'}$ and $R^{3'}$ are hydrogen; or 3) $R^1$ is methyl, ethyl, propyl or butyl; $R^{4'}$ is methyl; and $R^{2'}$ and $R^{3'}$ are hydrogen.

Particularly preferred examples of the at least one iodide salt are 1-ethyl-3-methylimidazolium iodide (emim I), 1-propyl-3-methylimidazolium iodide (pmim I), 1-butyl-3-methyl-imidazolium iodide (bmim I), 1-hexyl-3-methylimidazolium iodide (hmim I), 1,3-dimethyl-imidazolium iodide (mmim I), 1-allyl-3-methylimidazolium iodide (amim I), N-butyl-N-methyl-pyrrolidinium iodide (bmpl I) or N,N-dimethyl-pyrrolidinium iodide (mmpl I).

The amount of redox active species, in particular oxidant, present in an electrolyte formulation can range from 0.2 mM to 2 M, 1 mM to 500 Mm or from 5 mM to 200 mM. It should be understood that there is no necessary upper limit for the concentration of reductant species as long as it is soluble in the electrolyte formulation and does not excessively influence the viscosity of the formulation, or its function, in case of ordinary DSSC when an n-type semiconductor, e.g. TiO$_2$, is employed. An exemplary oxidant would include e.g. triiodide.

In a preferred embodiment, the electrolyte formulation of the present invention further comprises at least one compound containing a nitrogen atom having non-shared electron pairs. Examples of such compounds are found in EP 0 986 079 A2, starting on page 2, lines 40-55, and again from page 3, lines 14 extending to page 7, line 54, which are expressly incorporated herein by reference.

The compound containing a nitrogen atom having non-shared electron pairs can be a compound of the Formula (VI) and having a molecular weight of 1000 or less

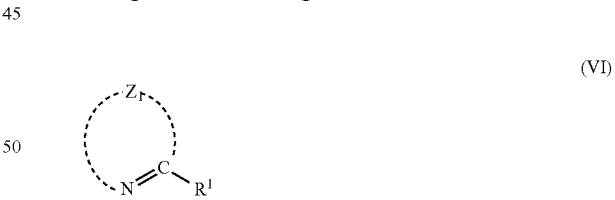

wherein:
$R_1$ represents an alkyl group, a cycloalkyl group, an aralkyl group, an aryl group, a heterocyclic group, an alkoxy group, an aryloxy group or an acylamino group; and
$Z_1$ represents an atomic group necessary to form a 5- or 6-membered aromatic ring together with the nitrogen atom and the carbon atom.

In some embodiments of the invention $R_1$ is selected from the group consisting of an alkyl group, a cycloalkyl group, an arylalkyl group, an aryl group, a heterocyclic group, an alkoxy group, an aryloxy group and an acylamino group. The alkyl group of $R_1$ may be either straight or branched and substituted or unsubstituted and preferably contains 1 to 20 carbon atoms. Examples of suitable alkyl groups include methyl, ethyl, propyl, isopropyl, butyl, t-butyl, 3-pentyl, hexyl, heptyl, 2-ethylhexyl, undecyl, dodecyl, chloromethyl, trifluoroethyl, hydroxyethyl, acetoxyethyl, propoxyethyl, isopropyloxyethyl, hydroxypropyl, acetoxypropyl, benzoyloxypropyl, ethoxypropyl, and butoxypropyl groups. The cycloalkyl group may be substituted or unsubstituted and may be a condensed ring. Preferred cycloalkyl groups are those containing 3 to 20 carbon atoms, such as cyclohexyl and cyclopentyl groups. The aralkyl group may be substituted or unsubstituted. The aryl moiety may be a condensed ring, and the alkylene moiety may be straight or branched. Preferred arylalkyl groups are those containing 7 to 27 carbon atoms, such as benzyl, 4-butoxybenzyl and phenethyl groups. The aryl group may be substituted or unsubstituted and may be a condensed ring. Preferred aryl groups are those containing 6 to 26 carbon atoms, such as phenyl, 2-naphthyl, 4-methoxyphenyl, and 3-chlorophenyl groups. The heterocyclic group may be substituted or unsubstituted and may have a condensed ring. Preferred heterocyclic groups are those containing 2 to 20 carbon atoms, such as 2-pyridyl, 4-pyridyl, 2-pyrimidyl, 1-methyl-2-imidazolyl, and 3-imidazolyl groups. The alkoxy group may be substituted or unsubstituted, and the alkyl moiety thereof may be straight or branched. Preferred alkoxy groups are those containing 1 to 20 carbon atoms, such as methoxy, ethoxy, butoxy, isopropyloxy, 2-ethylhexyloxy, and benzyloxy groups. The aryloxy group may be substituted or unsubstituted, and the aryl moiety thereof may be a condensed ring. Preferred aryloxy groups are those containing 6 to 26 carbon atoms, such as phenoxy, 2-naphthoxy, and 4-methoxyphenoxy groups. The acylamino group preferably contains 1 to 20 carbon atoms. Examples of preferred acylamino groups include acetylamino, valerylamino, and benzoylamino groups.

In some embodiments of the invention, $R_1$ preferably represents an alkyl group, an aralkyl group, an aryl group or an alkoxy group. An alkyl group and an aralkyl group are preferred as $R_1$.

In some embodiments, $Z_1$ represents an atomic group necessary to form a 5- or 6-membered aromatic ring together with the nitrogen and the carbon atoms. The aromatic ring is preferably formed by at least one atom selected from the group consisting of carbon, hydrogen, nitrogen, oxygen, and sulfur. The aromatic ring made up of $Z_1$, nitrogen, and carbon may have a condensed ring. Examples of preferred aromatic rings include pyridine, pyrimidine, pyrazine, pyridazine, quinoline, benzimidazole, triazine, imidazole, oxazole, thiazole, thiadiazole, triazole, and pyrazole rings. Pyridine, pyrimidine, pyrazine, quinoline, imidazole, and oxazole rings are still preferred, with pyridine and imidazole rings being particularly preferred. A pyridine ring is the most preferred. These aromatic rings may have other substituents, such as an alkyl group, in addition to $R_1$.

$R_1$ on a pyridine ring is preferably an alkyl group or a benzyl group, or more preferably a methyl, ethyl, n-propyl, 3-pentyl, isopropyloxyethyl, propyloxyethyl or benzyl group. $R_1$ on an imidazole ring is preferably an alkyl group or an aryl group, or more preferably a methyl, ethyl, isopropyl, undecyl or phenyl group.

The compound of Formula (VI) can be used either individually or as a mixture of two or more thereof. Specific but non-limiting examples of a compound of Formula (VI) are depicted below.

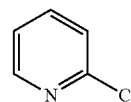

H-1

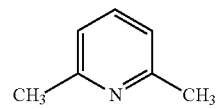

H-2

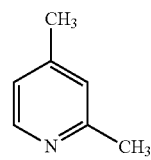

H-3

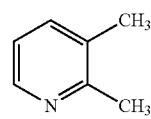

H-4

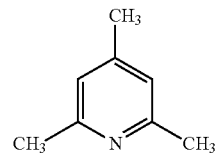

H-5

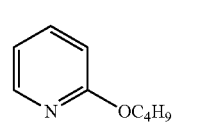

H-6

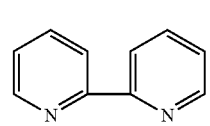

H-7

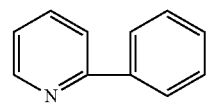

H-8

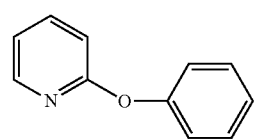

H-9

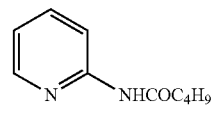

H-10

H-11

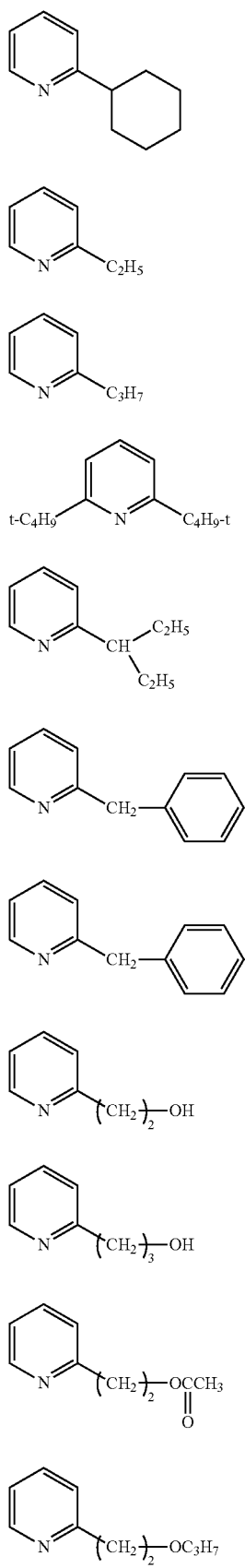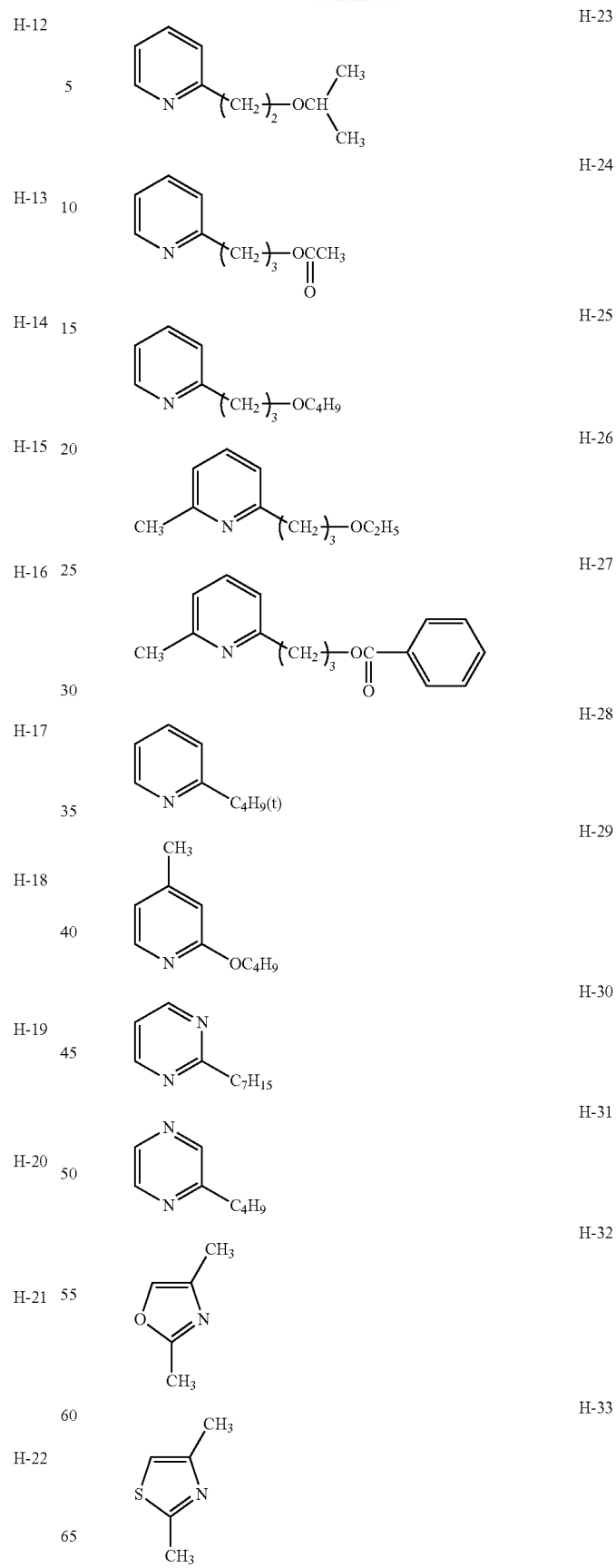

H-34 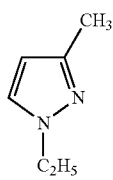

H-35 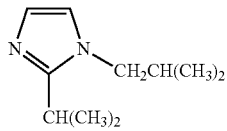

H-36 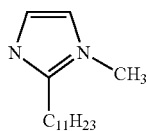

H-37 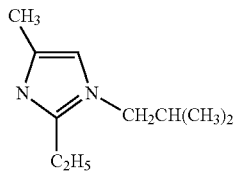

H-38 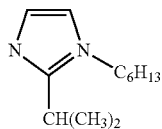

H-39 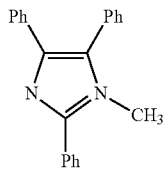

H-40 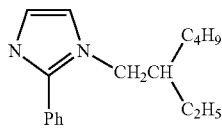

H-41 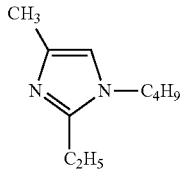

H-42 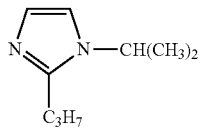

H-43 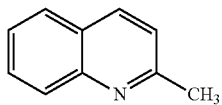

H-44 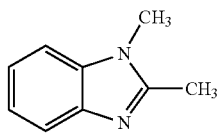

H-45 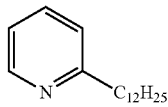

Preferred examples of compounds containing a nitrogen atom having non-shared electron pairs include imidazole and its derivatives, particularly benzimidazole and its derivatives.

The amount of compounds containing a nitrogen atom having non-shared electron pairs present in an electrolyte formulation can range from 0.01 to 5 weight %, from 0.05 to 2 weight % or from 0.1 to 1 weight %, based upon the total final weight of the electrolyte formulation containing all of its components or ingredients.

The electrolyte formulation of the present invention comprises less than 50 vol. % of an organic solvent. Preferably, the electrolyte formulation comprises less than 40%, more preferably less than 30%, still more preferably less than 20% and even less than 10%. Most preferably, the electrolyte formulation comprises less than 5% of an organic solvent. In some embodiments, the electrolyte formulation excludes or is substantially free of an organic solvent. Percentages are indicated on the basis of weight %, i.e. weight of the final formulation.

Organic solvents, if present in such amounts as indicated above, may be selected from those disclosed in the literature. Preferably, the solvent, if present, has a boiling point higher than 160 degrees centigrade, more preferably higher than 190 degrees C. Suitable solvents include, for example, propylene carbonate, ethylene carbonate, butylene carbonate, γ-butyrolactone, γ-valerolactone, glutaronitrile, adiponitrile, N-methyloxazolidinone, N-methylpyrrolidinone, N,N'-dimethylimidazolidinone, N,N-dimethylacetamide, cyclic ureas preferably 1,3-dimethyl-2-imidazolidinone or 1,3-dimethyl-3,4,5,6-tetrahydro-2(1H)-pyrimidinone, glymes preferably tetraglyme, sulfolane, sulfones which are preferably asymmetrically substituted such as 2-ethanesulfonyl-propane, 1-ethanesulfonyl-2-methyl-propane or 2-(propane-2-sulfonyl)-butane, 3-methylsulfolane, dimethylsulfoxide, trimethylphosphate diethylsulfoxide, triethylphosphate and methoxy-substituted nitriles. Other useful solvents are acetonitrile, benzonitrile and or valeronitrile.

If a solvent is present in the electrolyte formulation, there may further be comprised a polymer as gelling agent, wherein the polymer is polyvinylidenefluoride, polyvinylidene-hexafluoropropylene, polyvinylidene-hexafluoropropylene-chlorotrifluoroethylene copolymers, nafion, polyethylene oxide, polymethylmethacrylate, polyacrylonitrile, polypropylene, polystyrene, polybutadiene, polyethyleneglycol, polyvinylpyrrolidone, polyaniline, polypyrrole, polythiophene. The purpose of adding these polymers to electrolyte formulations is to make liquid electrolytes into quasi-solid or solid electrolytes, thus improving solvent retention, especially during aging.

The amount of polymer present in an electrolyte formulation can range from 0.02 to 25 weight %, from 0.1 to 10 weight % or from 0.2 to 5 weight %, based upon the total final weight of the electrolyte formulation containing all of its components or ingredients.

Polymer can be included in the electrolyte formulation regardless of whether or not solvent is present. The type and physical properties of polymer may be related to the amount (concentration) of polymer present in the electrolyte formulation. Typically a higher molecular weight polymer will have a higher viscosity and a lower moleculare weight polymer will have a lower viscosity. Likewise, a solvent can be included in the electrolyte formulation regardless of whether or not a polymer is present. When a polymer and solvent are included in the electrolyte formulation, the weight ratio of polymer to solvent can be varied as needed to provide an electrolyte formulation having the desired properties, e.g. a desired viscosity.

The electrolyte formulation of the invention may further comprise metal oxide nanoparticles like $SiO_2$, $TiO_2$, $Al_2O_3$, MgO or ZnO, for example, which are also capable of increasing solidity of the formulation and thus solvent retention.

The amount of metal oxide present in an electrolyte formulation can range from 0.02 to 25 weight %, from 0.1 to 10 weight % or from 0.2 to 5 weight %, based upon the total final weight of the electrolyte formulation containing all of its components or ingredients.

A metal oxide can be included in the electrolyte formulation regardless of whether or not a solvent is present The type and physical properties of metal oxide may be related to the amount (concentration) of metal oxide present in the electrolyte formulation. Likewise, a solvent can be included in the electrolyte formulation regardless of whether or not a metal oxide is present. When a metal oxide and solvent are included in the electrolyte formulation, the weight ratio of metal oxide to solvent can be varied as need to provide an electrolyte formulation having the desired properties.

Quantum dot-sensitized solar cells are disclosed in U.S. Pat. No. 6,861,722, for example. In dye-sensitized solar cells, a dye is used to absorb the sunlight to convert into the electrical energy. There are no restrictions per se with respect to the choice of the dye as long as the LUMO energy state is marginally above the conduction bandedge of the photoelectrode to be sensitized. Examples of dyes are disclosed in EP 0 986 079 A2, EP 1 180 774 A2 or EP 1 507 307 A1.

Preferred dyes are organic dyes such as MK-1, MK-2 or MK-3 (its structures are described in FIG. 1 of N. Koumura et al, J. Am. Chem. Soc. Vol 128, no. 44, 2006, 14256-14257), D102 (CAS no. 652145-28-3), D-149 (CAS no. 786643-20=7), D205 (CAS no. 936336-21-9), YD-2 as described in T. Bessho et al, Angew. Chem. Int. Ed. Vol 49, 37, 6646-6649, 2010, Y123 (CAS no. 1312465-92-1), bipyridine-Ruthenium dyes such as N3 (CAS no. 141460-19-7), N719 (CAS no. 207347-46-4), Z907 (CAS no. 502693-09-6), C101 (CAS no. 1048964-93-7), C106 (CAS no. 1152310-69-4), K19 (CAS no. 847665-45-6) or terpyridine-Ruthenium dyes such as N749 (CAS no. 359415-47-7).

The MK1, MK2 and MK3 dyes can be described according to the following chemical structure, wherein: a) for MK1, R is $C_6H_{13}$ and n is 3; b) for MK2, R is $C_6H_{13}$ and n is 4; and c) for MK3, R is H and n is 3:

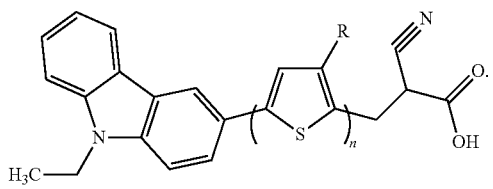

Particularly preferred dyes are Z907 or Z907Na, both of which are an amphiphilic ruthenium sensitizer, or D205.

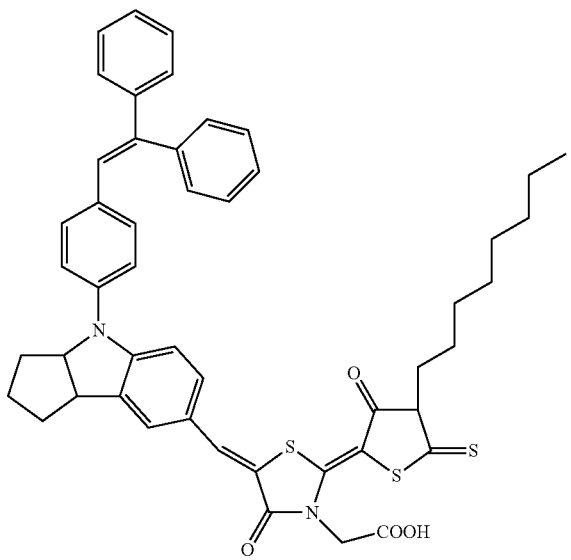

D205

In a preferred embodiment, the dye is coadsorbed with a phosphinic acid. A preferred example of a phosphinic acid is bis(3,3-dimethyl-butyl)-phosphinic acid (DINHOP) as disclosed in M. Wang et al, Dalton Trans., 2009, 10015-10020.

Particularly preferred dyes are Z907 or Z907Na. The dye Z907Na means $NaRu(2,2'$-bipyridine-4-carboxylic acid-4'-carboxylate$)(4,4'$-dinonyl-2,2'-bipyridine$)$-$(NCS)_2$ and it is the sodium salt of Z907. Other names include Ruthenizer 520-DN, cis-dithiocyanato-(2,2'-bipyridyl-4,4'-dicarboxylic acid-(2,2'-bipyridyl-4,4'-dinonyl)ruthenium (11), and cis-Bis (isothiocyanato)(2,2'-bipyridyl-4,4'-dicarboxylato)(4,4'-dinonyl-2'-bipyridyl)ruthenium(II).

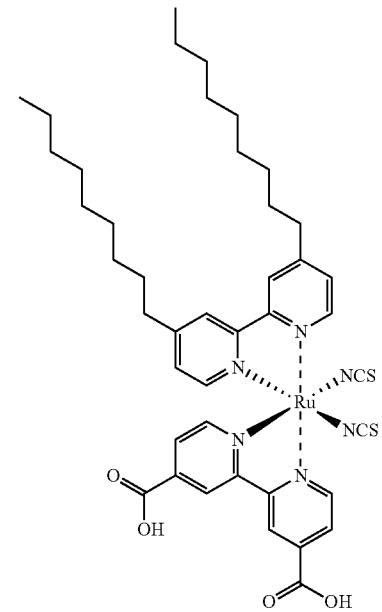

Z907

For example, a dye-sensitized solar cell comprises a photoelectrode, a counter electrode and, between the photoelectrode and the counterelectrode, an electrolyte formulation or a charge transporting material, and wherein a sensitizing dye is absorbed on the surface of the photoelectrode, on the side facing the counterelectrode.

According to a preferred embodiment of the device according to the invention, it comprises a semiconductor, the electrolyte formulation as described above and a counter electrode.

According to a preferred embodiment of the invention, the semiconductor is based on material selected from the group of Si, $TiO_2$, $SnO_2$, $Fe_2O_3$, $WO_3$, ZnO, $Nb_2O_5$, CdS, ZnS, PbS, $Bi_2S_3$, CdSe, GaP, InP, GaAs, CdTe, $CuInS_2$, and/or $CuInSe_2$. Preferably, the semiconductor comprises a mesoporous surface, thus increasing the surface optionally covered by a dye and being in contact with the electrolyte. Preferably, the semiconductor is present on a glass support or plastic or metal foil. Preferably, the support is conductive.

The device of the present invention preferably comprises a counter electrode. For example, fluorine doped tin oxide or tin doped indium oxide on glass (FTO- or ITO-glass, respectively) coated with Pt, carbon of preferably conductive allotropes, polyaniline or poly(3,4-ethylenedioxythiophene) (PEDOT). Metal substrates such as stainless steel or titanium sheet may be possible substrates beside glass.

The device of the present invention may be manufactured as the corresponding device of the prior art by simply replacing the electrolyte by the electrolyte formulation of the present invention. For example, in the case of dye-sensitized solar cells, device assembly is disclosed in numerous patent literature, for example WO 91/16719 (examples 34 and 35), but also scientific literature, for example in Barbé, C. J., Arendse, F., Comte, P., Jirousek, M., Lenzmann, F., Shklover, V., Gratzel, M. J. Am. Ceram. Soc. 1997, 80, 3157; and Wang, P., Zakeeruddin, S. M., Comte, P., Charvet, R., Humphry-Baker, R., Gratzel, M. J. Phys. Chem. B 2003, 107, 14336.

Unlike electrochemical devices which require much more power density such as capacitors the DSC does not require high conductivity of the liquid electrolyte. For example in DSC, the electrode resistance of electrolyte at 10° C. is estimated by semiconductor electrode thickness divided by electrolyte conductivity, typically at 10 μm/10 mScm$^{-1}$=0.01 Ωcm$^2$.

Preferably, the sensitized semiconducting material serves as a photoanode. Preferably, the counter electrode is a cathode.

The present invention provides a method for preparing a photoelectric cell comprising the step of bringing the electrolyte formulation of the invention in contact with a surface of a semiconductor, said surface optionally being coated with a sensitizer. Preferably, the semiconductor is selected from the materials given above, and the sensitizer is preferably selected from quantum dots and/or a dye as disclosed above, particularly preferably selected from a dye.

Preferably, the electrolyte formulation may simply be poured onto the semiconductor. Preferably, it is applied to the otherwise completed device already comprising a counter electrode by creating a vacuum in the internal lumen of the cell through a hole in the counter electrode and adding the electrolyte formulation as disclosed in the reference of Wang et al., J. Phys. Chem. B 2003, 107, 14336.

Exemplary electrolyte formulations useful in optoelectronic or electrochemical devices can be summarized as follows.

| Ingredient | Exemplary Formulations (molar ratio) | | | |
|---|---|---|---|---|
|  | I | II | III | IV |
| Compound Formula (I) (1st) | 1-100 | 10-90 | 10-90 | 10-90 |
| Compound Formula (I) (2nd) | 99-0 | 10-90 |  |  |
| Compound Formula (II) | 99-0 |  |  |  |
| Compound Formula (III) | 99-0 |  |  |  |
| Further Salt (1st) | 99-0 | 90-10 | 90-10 |  |
| Further Salt (2nd) | 99-0 | 90-10 |  |  |
| Iodide Salt (1st) | 99-0 | 90-10 | 90-10 | 90-10 |
| Iodide Salt (2nd) | 99-0 | 90-10 | 90-10 | 90-10 |
| Iodine | 20-0 | 20-0 | 20-0 | 20-0 |
| Guanidinium thiocyanate | 10-0 | 10-0 | 10-0 | 10-0 |
| NBB | 20-0 | 20-0 | 20-0 | 20-0 |

| Ingredient | Exemplary Formulations (molar ratio) | | | |
|---|---|---|---|---|
|  | I | II | III | IV |
| Compound Formula (I) (1st) | 30-70 | 40-80 | 30-70 | 40-70 |
| Compound Formula (I) (2nd) |  |  | 70-0 | 70-0 |
| Further Salt (1st) |  |  | 70-0 | 70-0 |
| Further Salt (2nd) |  |  | 70-0 | 70-0 |
| Iodide Salt (1st) | 60-20 | 80-40 | 70-30 | 70-40 |
| Iodide Salt (2nd) | 60-20 | 80-40 | 70-30 | 70-40 |
| Iodine | 20-1 | 20-1 | 20-1 | 20-1 |
| Guanidinium thiocyanate | 10-1 | 10-1 | 10-1 | 10-1 |
| NBB | 20-1 | 20-1 | 20-1 | 20-1 |

It should be understood that even if the tables above do not indicate the presence of a particular compound of class or type of compound, it can nonetheless be included in the electrolyte formulation as disclosed herein or as such compound is already employed in the art of electrolyte formulations.

The invention includes some embodiments, wherein: a) the compound of Formula (I) and one or more iodide salts are present in equivalent molar amounts; b) the compound of Formula (I) and two different iodide salts are present in equivalent molar amounts; c) the compound of Formula (I) is present in a molar excess over at least one iodide salt; d) the compound of Formula (I) is present in two times the molar amount of at least one iodide salt; or e) the molar amount of compound of Formula (I) is equivalent to the total molar amount of two different iodide salts.

The following examples include more narrowly defined electrolyte formulations. It should be understood that the ingredients in the exemplary formulations can be interchanged with any of the similar ingredients discussed herein.

In view of the above description and the examples below, one of ordinary skill in the art will be able to practice the invention as claimed without undue experimentation. The foregoing will be better understood with reference to the following examples that detail certain procedures for the preparation of embodiments of the present invention. All references made to these examples are for the purposes of illustration. The following examples should not be considered exhaustive, but merely illustrative of only a few of the many embodiments contemplated by the present invention. The present invention will now be illustrated, without limiting its scope, by way of the following examples.

Example 1

Synthesis, characterization and viscosity/conductivity measurements of 1-ethyl-3-methylimidzolium tetracyanoborate (emim TCB), 1-ethyl-3-methylimidzolium trifluorocyanoborate (emim TFCB) and 1-ethyl-3-methylimidzolium difluorodicyanoborate (emim DDB)

1-Ethyl-3-methylimidzolium tetracyanoborate and 1-ethyl-3-methylimidzolium difluorodicyanoborate are synthesized according to WO 2004/072089, examples 9 and 15.

1-ethyl-3-methylimidzolium trifluorocyanoborate (emim TFCB) is synthesized as follows

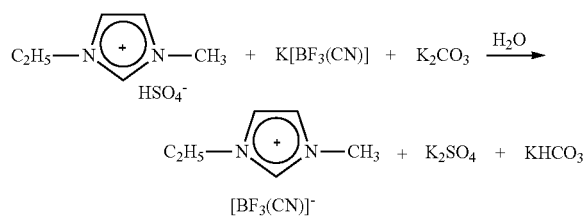

1-Ethyl-3-methylimidazolium hydrogen sulfate (18.6 g, 89.3 mmol) is dissolved in ca. 100 ml of water. The solution is cooled down with addition of ca. 80 g of ice and neutralized by addition of 12.1 g (87.5 mmol) of $K_2CO_3$ in 50 ml of water. After addition of 11.75 g (88.4 mmol) of $K[BF_3CN]$ the reaction mixture is left stirring at 0° C. for 10 min. The product, 1-ethyl-3-methylimidazolium trifluorocyanoborate, emim $[BF_3CN]$ is extracted three times with dichloromethane. Combined organic phases are dried with $Na_2SO_4$ and the solvent is removed via distillation. The residue is dried in vacuum (ca. $10^{-3}$ mbar) and 4.0 g (22%) of 1-ethyl-3-methylimidzolium trifluorocyanoborate (emim TFCB) is obtained. The product is characterized by NMR spectroscopy:

$^{11}$B NMR (128.3776 MHz) (Solvent: $CD_3CN$; Reference: $BF_3 \cdot Et_2O$) δ, ppm: −3.7 q, $^1J_{F,B}$=26.8 Hz;
$^{19}$F NMR (376.4984 MHz) (Solvent: $CD_3CN$; Reference: $CCl_3F$) δ, ppm: −137.4 q, $^1J_{F,B}$=27 Hz;
$^1$H NMR (400.1300 MHz) (Solvent: $CD_3CN$; Reference: TMS) δ, ppm: 8.47 br.s (CH); 7.43 d,d (CH), $J_{H,H}$=1.8 Hz; 7.37 d,d (CH), $J_{H,H}$=1.8 Hz; 4.20 q (2H, $CH_2$), 3.86 (3H, $CH_3$); 1.48 t (3H, $CH_3$), $^3J_{H,H}$=7.3 Hz.

Table 1 gives specific parameters of the ionic liquids used:

| Compound | T (° C.) | Density (g/cm$^3$) | Dynamic viscosity (mPa/s) | Specific conductivity (mS/cm) |
|---|---|---|---|---|
| emim TCB* | 20 | 1.04 | 22.2 | 13.0 |
|  | 40 | 1.03 | 11.2 | 23.2 |
|  | 60 | 1.01 | 6.75 | 35.9 |
|  | 80 | 1.00 | 4.53 | 50.5 |
| emim DDB | 20 | 1.12 | 11.1 | 28.4 |
|  | 40 | 1.10 | 7.13 | 41.6 |
|  | 60 | 1.09 | 4.95 | 56.7 |
|  | 80 | 1.08 | 3.65 | 72.5 |
| emim TFCB* | 20 | 1.19 | 14.7 |  |
|  | 40 | 1.17 | 9.21 |  |
|  | 60 | 1.16 | 6.29 |  |
|  | 80 | 1.14 | 4.58 |  |

*not according to the invention

Example 2

Synthesis of 1-butyl-1-methylpyrrolidinium difluorodicyanoborate (bmpl DDB)

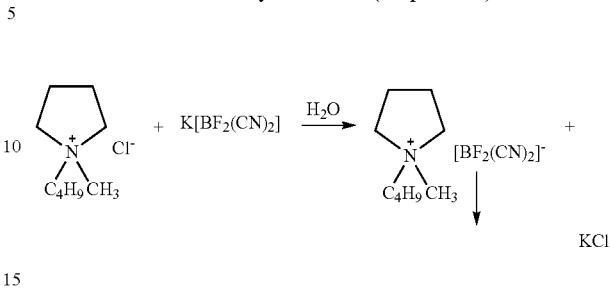

9.0 g (64.3 mmol) of potassium difluoro-dicyanoborate is added to the solution of 11.43 g (64.3 mmol) of 1-butyl-1-methylpyrrolidinium chloride in 30 ml of water at room temperature. The reaction mixture is stirred at room temperature for 30 min and extracted with two portions of dichloromethane. The organic phase is separated and washed with cold water. The organic solvent is evaporated and the residue is dried in vacuum at 70° C. 14.65 g (94%) of transparent, practically colourless liquid is obtained which is 1-butyl-1-methylpyrrolidinium difluorodicyanoborate. The product is characterised by NMR spectroscopy.

1H NMR (d6-DMSO): δ=3.44 (m, 4H), 3.29 (m, 2H), 2.98 (s, 3H), 2.09 (m, 4H), 1.69 (m, 2H), 1.33 (m, 2H), 0.94 (t, $J_{(H,H)}$=6.8 Hz, 3H).

Example, 3

Formulations and Device

The following electrolyte formulations are synthesized to demonstrate the unexpected advantage of electrolyte formulations according to the invention relative to electrolyte formulations of the prior art containing emim TCB or emim TFCB.

The electrolyte formulations are prepared through mixing of one or more of 1,3-dimethylimidazolium iodide (mmimI), 1-ethyl-3-methylimidazolium iodide (emimI) and 1-methyl-3-propylimidazolium iodide (mpimI), 1,1-dimethylpyrrolidinium iodide (mmpII), iodine, N-butylbenzimidazole (NBB) and guanidinium thiocyanate (guaSCN) and the corresponding ionic liquid such as emimDDB, bmpIDDB according to the invention or emimTCB, bmpITCB or emimTFCB according to the prior art in the molar ratio as listed below. It may be necessary to apply heat up to 120° C. to make the electrolyte formulation homogeneous. Care has to be taken for emim TFCB because this anion of the prior art is fragile to heat stress which is another disadvantage for an application in dye-sensitized solar cells.

Electrolyte formulation A given in molar ratio: 36 mmimI, 36 emimI, 5 $I_2$, 48 emimTCB, 2 guaSCN, 10 NBB;
Electrolyte formulation B given in molar ratio: 36 mmimI, 36 emimI, 5 $I_2$, 48 emimDDB, 2 guaSCN, 10 NBB;
Electrolyte formulation C given in molar ratio: 36 mmimI, 36 emimI, 5 I2, 48 emimTFCB, 2 guaSCN, 10 NBB;
Electrolyte formulation D given in molar ratio: 60 emimI, 5 $I_2$, 60 bmpITCB, 2 guaSCN, 10 NBB;
Electrolyte formulation E given in molar ratio: 60 emimI, 5 $I_2$, 60 bmpIDDB, 2 guaSCN, 10 NBB;
Electrolyte formulation F given in molar ratio: 60 mmpII, 5 $I_2$, 60 emimTCB, 2 guaSCN, 10 NBB;

Electrolyte formulation G given in molar ratio: 60 mmpII, 5 $I_2$, 60 emimDDB, 2 guaSCN, 10 NBB.

TABLE 2

Electrolyte formulations employed in the present invention.

| Electrolyte formulation | DSC efficiency at 25° C. under AM1.5 |
|---|---|
| A* | 5.3% ± 0.5% |
| B | 6.0% ± 0.4% |
| C* | less than 4.8% |
| D* | 2.0% ± 0.4% |
| E | 2.6% ± 0.2% |
| F* | 1.7% ± 0.1% |
| G | 1.9% ± 0.1% |

*not according to the invention

Table 2 establishes that electrolytes comprising DDB as anion always perform better than electrolytes comprising TCB as anion if the same cation is used.

The compounds mmimI, emimI, mmpII, mpimI, $I_2$, NBB and guaSCN are commercially available or are synthesized according to known literature such as Bonhote, P et al. *Inorg. Chem.* 1996, 35, 1168-1178.

The dye-sensitized solar cells are fabricated as disclosed in U.S. Pat. No. 5,728,487 or WO 2007/093961 as follows.

A double-layer, mesoporous $TiO_2$ electrode was prepared as disclosed in Wang P et al., J. Phys. Chem. B 2003, 107, 14336, in particular page 14337, in order to obtain a photoanode consisting of a double layer structure. To prepare a transparent nanoporous $TiO_2$ electrode, a screen printing paste containing terpineol solvent and nanoparticulate $TiO_2$ of anatase phase with 20 nm diameter was deposited on a transparent conductive substrate to 5 mm×5 mm squared shape by using a hand printer. The paste was dried for 10 minutes at 120 degrees Celsius. Another screen printing paste containing $TiO_2$ with 400 nm diameter was then deposited on top of the nanoporous layer to prepare an opaque layer. The double layer film was then sintered at 500 degrees Celsius for an hour with the result of an underlying transparent layer (7 microns thick) and a top opaque layer (4 microns thick). After sintering, the electrode was immersed in 40 mM aqueous solution of $TiCl_4$ (Merck) for 30 minutes at 70 degrees Celsius and then rinsed with pure water sufficiently. Thus $TiCl_4$-treated electrode was dried at 500 degrees Celsius for 30 minutes just before dye sensitization. The electrode was dipped into a 0.3 mM Z907 dye solution of acetonitrile (Merck HPLC grade) and tert-butyl alcohol (Merck), v:v=1:1 for 60 hours at 19 degrees Celsius. The counter electrode was prepared with thermal pyrolysis method as disclosed in the reference above. A droplet of 5 mM solution of platinic acid (Merck) was casted at 8 μl/cm2 and dried on a conductive substrate. The dye-sensitized solar cell was assembled by using 30 micron thick Bynel (DuPont, USA) hot-melt film to seal up by heating. The internal space was filled with each of the electrolyte formulations as described above to produce the corresponding devices.

The dye Z907 is an amphiphilic ruthenium sensitizer Ru(2, 2'-bipyridine 4,4'-dicarboxylic acid) (4,4'-dinonyl-2,2'-bipyridine)(NCS)$_2$ or [Ru(H2dcbpy)(dnbpy)(NCS)$_2$].

Example 4

Characteristics of the Dye-Sensitized Solar Cells According to Example 3

The measurements of photocurrent-voltage curves are carried out under Air Mass 1.5 simulated sunlight (AM 1.5) with temperature control. A photomask of 4 mm×4 mm is placed on top of the devices fabricated according to example 3 to define the light projection area. The cell gap is in the range of 25 to 30 micron.

Energy conversion efficiency is generally the ratio between the useful output of an energy conversion machine and the input of light radiation, in energy terms, determined by using adjustable resistant load to optimize the electric power output.

FIG. 1 shows the photocurrent density-voltage curves for device A containing the electrolyte formulation A which form the basis for table 2 at 10° C., 25° C., 42° C. and 57° C.

Figure 2:
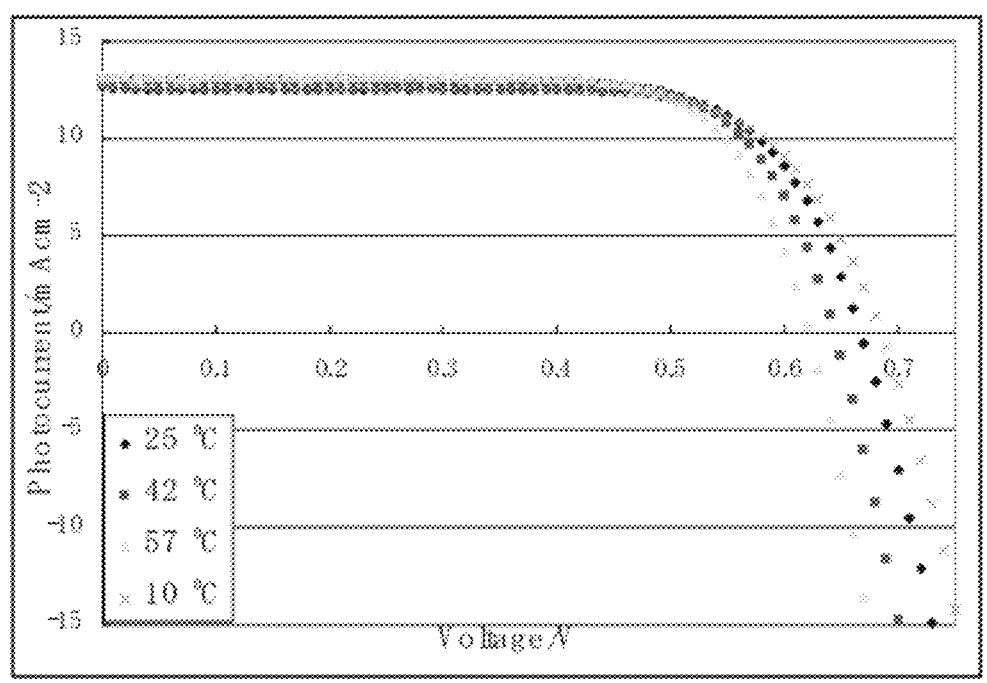
FIG. 2 depicts the photocurrent density-voltage curves for device B containing the electrolyte formulation B according to the invention which curves form the basis for table 2 at 10° C., 25° C., 42° C. and 57° C.

FIG. 2 shows the photocurrent density-voltage curves for device B containing the electrolyte formulation B according to the invention which form the basis for table 2 at 10° C., 25° C., 42° C. and 57° C.

Figure 3:
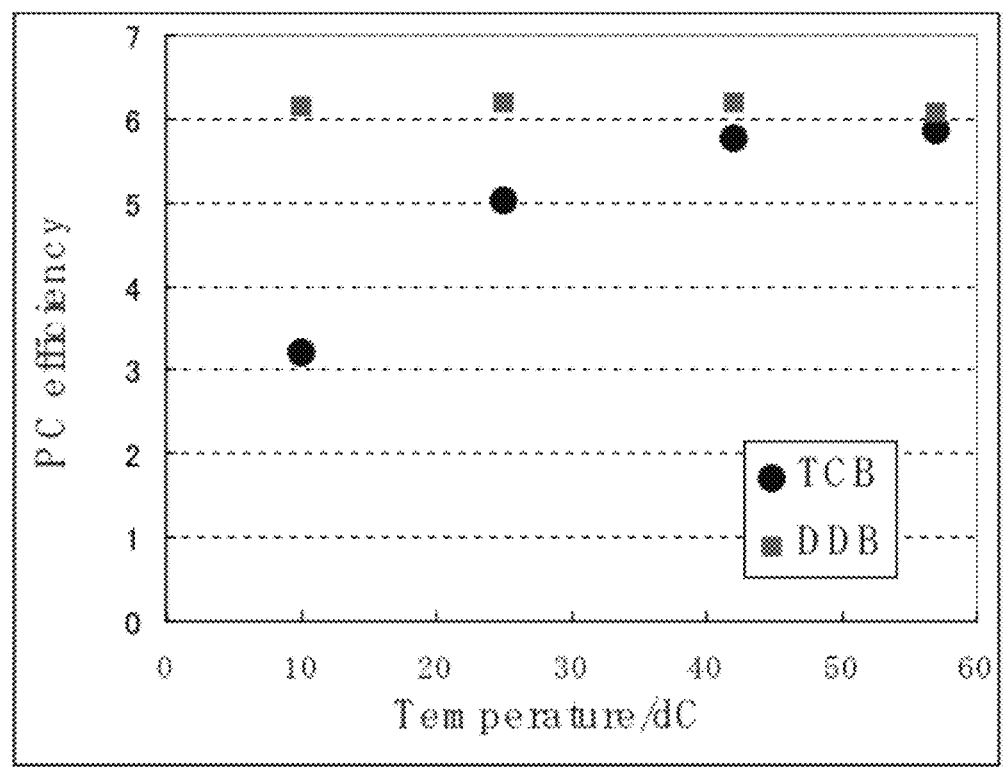
FIG. 3 depicts a plot of Temperature/dc versus PC efficiency and a summary of the data of FIGS. 1 and 2 establishing that the electrolyte formulations according to the invention (for example, emim DDB) demonstrate better performance at low temperatures than the prior art device A with emim TCB.

FIG. 3 gives a summary of the data of FIGS. 1 and 2 documenting that the electrolyte formulations according to the invention (emim DDB) show a better performance at low temperatures than the prior art device A with emim TCB.

Example 5

Electrochemical Impedance Spectroscopy (EIS)

The impedance of the devices A and B fabricated according to example 3 are measured at 10° C. and 25° C. under AM1.5 by using Gamry R600 impedance analyzer to identify the factor responsible for the photovoltaic performance differences.

Figure 4:
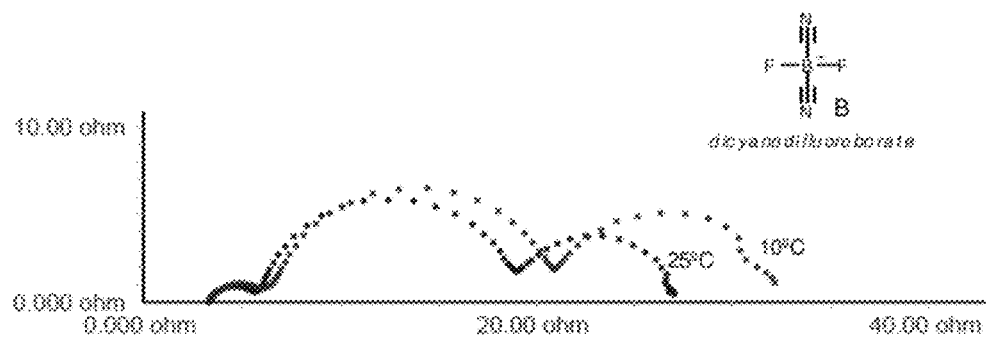
FIG. 4 depicts the impedance spectrum of device B containing electrolyte formulation B.

FIG. 4 gives the impedance spectrum of device B containing electrolyte formulation B.

Figure 5:
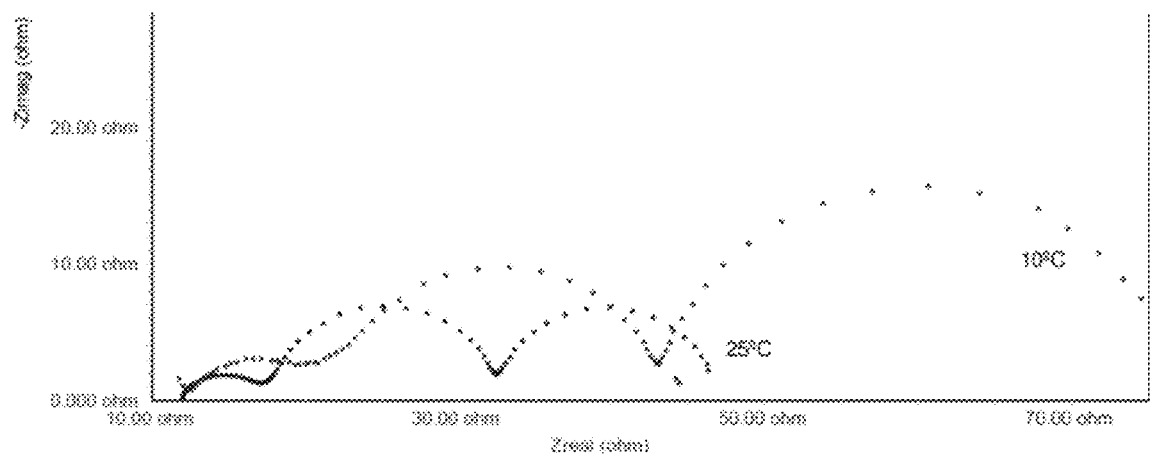
FIG. 5 depicts the impedance spectrum of device A containing electrolyte formulation A.
Figure 5:
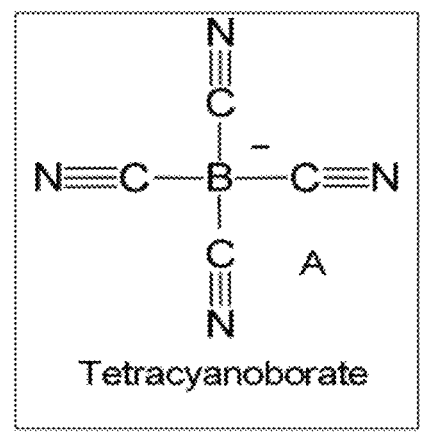

FIG. 5 gives the impedance spectrum of device A containing electrolyte formulation A.

Table 3 shows impedances and their characteristic frequencies for devices A and B measured at 10 and 25 degrees Celsius under AM1.5.

TABLE 3

| | Temperature/° C. | Charge Transfer Resistance | | Nernst Diffusion Resistance | |
|---|---|---|---|---|---|
| | | $Z_{CT}$ (Ω) | $f_{CT}$ (Hz) | $Z_{ND}$ (Ω) | $f_{ND}$ (Hz) |
| A | 10 | 6 | 1.0E+04 | 37.3 | 4.5E−02 |
| | 25 | 4.2 | 2.5E+04 | 16.5 | 8.0E−02 |
| B | 10 | 2.5 | 2.5E+04 | 12.1 | 1.0E−01 |
| | 25 | 2 | 3.2E+04 | 9.1 | 1.8E−01 |

It can be seen that replacement of TCB with DDB reduces both charge transfer resistance at counter electrode and Nernst diffusion resistance for oxidant migration significantly making DDB-based DSC work at 10 degrees Celsius.

Example 6

Preparation of Electrolyte Formulations

The following electrolyte formulations are synthesized according to example 3 and used as electrolytes in DSSC test cells as prepared according to example 3:

Electrolyte formulation H given in molar ratio: 36 mmimI, 36 emimI, 5 $I_2$, 72 bmpI TCB, 2 guaSCN, 10 NBB;

Electrolyte formulation J given in molar ratio: 36 mmimI, 36 emimI, 5 $I_2$, 72 bmpI DDB, 2 guaSCN, 10 NBB.

Table 4 summarizes the results of the measurements of the above cited electrolyte formulations according to example 4: η=DSC efficiency.

TABLE 4

| Electrolyte | $J_{sc}$ (mAcm$^{-2}$) | $V_{OC}$ (V) | FF | η (%) |
|---|---|---|---|---|
| H* | 8.18 | 0.70 | 0.58 | 3.47 |
| H* | 8.55 | 0.75 | 0.55 | 3.48 |
| J | 8.22 | 0.75 | 0.66 | 4.11 |
| J | 8.20 | 0.76 | 0.65 | 4.08 |

*not according to the invention

As used herein and unless otherwise specified, the term "about" or "approximately" are taken to mean±10%, ±5%, ±2.5% or ±1% of a specified valued. As used herein and unless otherwise specified, the term "substantially" is taken to mean "to a large degree", "at least a majority of", greater than 70%, greater than 85%, greater than 90%, greater than 95%, greater than 98% or greater than 99%.

As used herein, the term derivative means a chemical substance related structurally to and derived (theoretically derived) from a parent substance. In other words, a derivative is a compound that is formed from a similar parent compound or a compound that can be imagined to arise from a parent compound, if one or more atoms of the parent compound are replaced with another atom or group of atoms. A derivative is also a compound derived or obtained from a parent compound and containing essential elements of the parent substance. A derivative may be produced from a parent compound of similar structure in one or more steps. In each case, there has to be a substantial chemical structure similarity between the parent compound and the derivative.

The above is a detailed description of particular embodiments of the invention. It will be appreciated that, although specific embodiments of the invention have been described herein for purposes of illustration, various modifications may be made without departing from the spirit and scope of the invention. Accordingly, the invention is not limited except as by the appended claims. All of the embodiments disclosed and claimed herein can be made and executed without undue experimentation in light of the present disclosure.

The invention claimed is:

1. An electrolyte formulation comprising at least one compound of the Formula (I)

$$Kt^+[B(CN)_2F_2]^- \quad (I)$$

in which Kt$^+$ is an organic cation selected from the group of

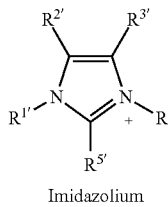
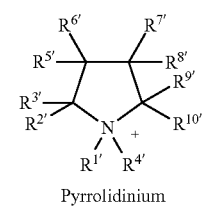

Imidazolium    Pyrrolidinium where the substituents R$^{1'}$ to R$^{10'}$ each, independently of one another, denote H with the assumption that R$^{1'}$ and R$^{4'}$ are not simultaneously H, straight-chain or branched alkyl having 1-20 C atoms, which optionally may be fluorinated, straight-chain or branched alkenyl having 2-20 C atoms and one or more double bonds, which optionally may be fluorinated, straight-chain or branched alkynyl having 2-20 C atoms and one or more triple bonds which optionally may be fluorinated or straight-chain or branched alkoxyalkyl having 2 to 8 C atoms, one or more redox couples, optionally one or more further salts, and optionally one or more constituents.

2. The electrolyte formulation of claim 1, wherein one or more further salts and one or more constituents are present, and wherein the formulation further comprises one or more components selected from the group consisting of guanidinium thiocyanate, one or more compounds containing a nitrogen atom having non-shared electron pairs, and n-butyl-benzimidazole.

3. The electrolyte formulation of claim 1 comprising one or more one or more compounds of the Formula (I), iodine, one or more iodide salts, guanidinium thiocyanate, and n-butyl-benzimidazole.

4. The electrolyte formulation of claim 1, wherein the one or more redox couples is one or more iodide salts comprising an organic cation that is:

a) the same as the cation Kt$^+$ of at least one compound of Formula (I) in the electrolyte formulation;

b) selected from Kt$^+$ as defined herein for at least one compound of Formula (I) in the electrolyte formulation;

c) an imidazolium cation of Formula (IV)

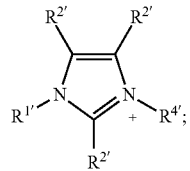

imidazolium d) an imidazolium cation of Formula (IV), wherein: 1) R$^{1'}$ is alkyl, allyl or alkenyl; R$^{4'}$ is alkyl, allyl or alkenyl; and R$^{2'}$ is hydrogen or alkyl; or 2) R$^{1'}$ is alkyl, allyl or alkenyl; R$^{4'}$ is alkyl; and R$^{2'}$ is hydrogen; or 3) R$^{1'}$ is C$_1$-C$_6$-alkyl or allyl; R$^{4'}$ is C$_1$-C$_2$-alkyl; and R$^{2'}$ is hydrogen; or 4) R$^{1'}$ is methyl, ethyl, propyl, butyl, pentyl, hexyl, or allyl; R$^{4'}$ is methyl; and R$^{2'}$ is hydrogen; or e) a pyrrolidinium cation of Formula (V)

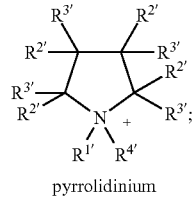

pyrrolidinium or f) a pyrrolidinium cation of Formula (V), wherein: 1) R$^{1'}$ is alkyl, allyl or alkenyl; R$^{4'}$ is alkyl, allyl or alkenyl; and R$^{2'}$ and R$^{3'}$ are hydrogen or alkyl; or 2) R$^{1'}$ is alkyl; R$^{4'}$ is alkyl; and R$^{2'}$ and R$^{3'}$ are hydrogen; or 3) R$^{1'}$ is methyl, ethyl, propyl or butyl; R$^{4'}$ is methyl; and R$^{2'}$ and R$^{3'}$ are hydrogen.

5. The electrolyte formulation of claim 4, wherein at least one iodide salt is selected from the group consisting of 1-ethyl-3-methylimidazolium iodide (emim I), 1-propyl-3-methylimidazolium iodide (pmim I), 1-butyl-3-methyl-imidazolium iodide (bmim I), 1-hexyl-3-methylimidazolium iodide (hmim I), 1,3-dimethyl-imidazolium iodide (mmim I), 1-allyl-3-methylimidazolium iodide (amim I), N-butyl-N-methyl-pyrrolidinium iodide (bmpl I) and N,N-dimethyl-pyrrolidinium iodide (mmpl I).

6. An electrolyte formulation comprising at least one compound of the Formula (I)

in which $Kt^+$ is an organic cation selected from the group of

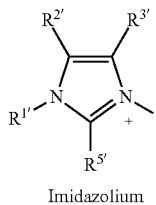 or 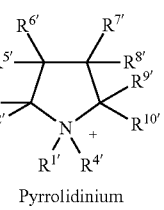

Imidazolium  Pyrrolidinium where the substituents
$R^{1'}$ to $R^{10'}$ each, independently of one another, denote
H with the assumption that $R^{1'}$ and $R^{4'}$ are not simultaneously H,
straight-chain or branched alkyl having 1-20 C atoms, which optionally may be fluorinated,
straight-chain or branched alkenyl having 2-20 C atoms and one or more double bonds, which optionally may be fluorinated,
straight-chain or branched alkynyl having 2-20 C atoms and one or more triple bonds which optionally may be fluorinated or straight-chain or branched alkoxyalkyl having 2 to 8 C atoms; wherein
a) the electrolyte formulation is a binary system comprising a compound of Formula (I) and a further salt;
b) the electrolyte formulation comprises one or more compounds of Formula (I), iodine and one or more iodide salts;
c) the electrolyte formulation comprises one or more compounds of Formula (I), iodine and two iodide salts;
d) the electrolyte formulation is a ternary system comprising a compound of Formula (I) and two further salts;
e) the electrolyte formulation comprises one or more guanidinium salts; and/or
f) the substituents $R^{2'}$, $R^{3'}$ and $R^{5'}$ to $R^{10'}$ are different.

7. The electrolyte formulation of claim 1 comprising at least one compound of the Formula (I)

in which $Kt^+$ is an organic cation selected from the group of

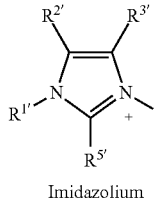 or 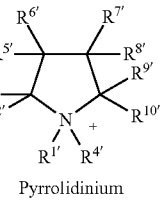

Imidazolium  Pyrrolidinium where the substituents
$R^{1'}$ to $R^{10'}$ each, independently of one another, denote
H with the assumption that $R^{1'}$ and $R^{4'}$ are not simultaneously H,
straight-chain or branched alkyl having 1-20 C atoms, which optionally may be fluorinated,
straight-chain or branched alkenyl having 2-20 C atoms and one or more double bonds, which optionally may be fluorinated,
straight-chain or branched alkynyl having 2-20 C atoms and one or more triple bonds which optionally may be fluorinated or
straight-chain or branched alkoxyalkyl having 2 to 8 C atoms; wherein
the formulation comprises less than 50% wt, less than 40% wt, less than 30% wt, less than 20% wt, less than 10% wt, less than 5% wt, or less than 1% wt of organic solvent or the electrolyte formulation excludes an organic solvent.

8. The electrolyte formulation of claim 1 comprising one or more compounds of the Formula (I)

in which $Kt^+$ is an organic cation selected from the group of

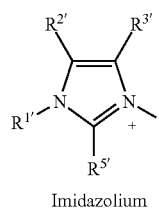 or 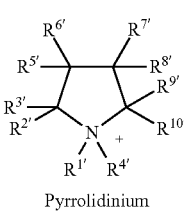

Imidazolium  Pyrrolidinium where the substituents
$R^{1'}$ to $R^{10'}$ each, independently of one another, denote
H with the assumption that $R^{1'}$ and $R^{4'}$ are not simultaneously H,
straight-chain or branched alkyl having 1-20 C atoms, which optionally may be fluorinated,
straight-chain or branched alkenyl having 2-20 C atoms and one or more double bonds, which optionally may be fluorinated,
straight-chain or branched alkynyl having 2-20 C atoms and one or more triple bonds which optionally may be fluorinated or
straight-chain or branched alkoxyalkyl having 2 to 8 C atoms;
and one or more constituents selected from the group consisting of: one or more further salts, one or more solvents, iodine, one or more iodide salts, one or more compounds containing a nitrogen atom having non-shared electron pairs, one or more redox active species, one or more polymers, one or more metal oxide nanoparticles, one or more dyes, guanidinium thiocyanate and a combination thereof.

9. The electrolyte formulation of claim 1 comprising at least one compound of the Formula (I)

in which $Kt^+$ is an organic cation selected from the group of

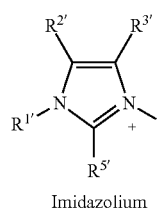 or 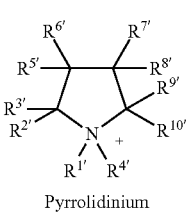

Imidazolium  Pyrrolidinium where the substituents
$R^{1'}$ to $R^{10'}$ each, independently of one another, denote
H with the assumption that $R^{1'}$ and $R^{4'}$ are not simultaneously H, straight-chain or branched alkyl having 1-20 C atoms, which optionally may be fluorinated, straight-chain or branched alkenyl having 2-20 C atoms and one or more double bonds, which optionally may be fluorinated, straight-chain or branched alkynyl having 2-20 C atoms and one or more triple bonds which optionally may be fluorinated or straight-chain or branched alkoxyalkyl having 2 to 8 C atoms; wherein the difluorodicyanoborate anion is present in the electrolyte formulation at a concentration ranging from 0.1 to 4 M or 0.8 to 3.5 M.

10. The electrolyte formulation of claim 1 comprising at least one compound of the Formula (I)

in which Kt$^+$ is an organic cation selected from the group of

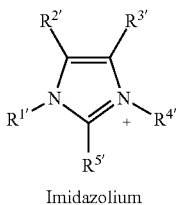 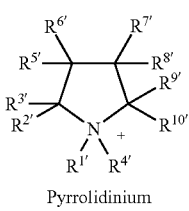

Imidazolium      Pyrrolidinium where the substituents
R$^{1'}$ to R$^{10'}$ each, independently of one another, denote
H with the assumption that R$^{1'}$ and R$^{4'}$ are not simultaneously H, straight-chain or branched alkyl having 1-20 C atoms, which optionally may be fluorinated, straight-chain or branched alkenyl having 2-20 C atoms and one or more double bonds, which optionally may be fluorinated, straight-chain or branched alkynyl having 2-20 C atoms and one or more triple bonds which optionally may be fluorinated or straight-chain or branched alkoxyalkyl having 2 to 8 C atoms; wherein the difluorodicyanoborate anion in the electrolyte formulation is present in molar excess over the organic cation Kt$^+$ of the compound of Formula (I).

11. An optoelectronic and/or electrochemical device comprising an electrolyte formulation of comprising at least one compound of Formula (I)

in which Kt$^+$ is an organic cation selected from the group of

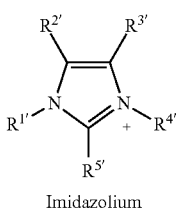 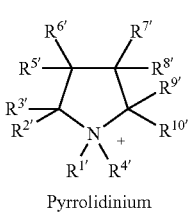

Imidazolium      Pyrrolidinium where the substituents
R$^{1'}$ to R$^{10'}$ each independently of one another denote
H with the assumption that R$^{1'}$ and R$^{4'}$ are not simultaneously H, straight-chain or branched alkyl having 1-20 C atoms which optionally may be fluorinated, straight-chain or branched alkenyl having 2-20 C atoms and one or more double bonds which optionally may be fluorinated, straight-chain or branched alkynyl having 2-20 C atoms and one or more triple bonds which optionally may be fluorinated or straight-chain or branched alkoxyalkyl having 2 to 8 C atoms.

12. The device of claim 11, wherein the device is selected from the group consisting of a photovoltaic cell, light emitting device, electrochromic device, photo-electrochromic device, electrochemical sensor, biosensor, double layer capacitor, electrochemical battery, quantum dot-sensitized solar cell, and dye-sensitized solar cell.

13. The device of claim 11 in which Kt$^+$ of the compound of Formula (I) is

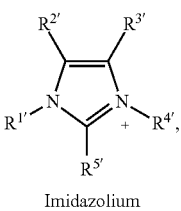

Imidazolium where the substituents R$^{2'}$ and R$^{3'}$ are H, R$^{5'}$ is H or straight-chain or branched alkyl having 1 to 4 C atoms and R$^{1'}$ and R$^{4'}$ are each independently of one another straight chain or branched alkyl having 1-20 C atoms or straight-chain or branched alkenyl having 3 C atoms.

14. The device of claim 11 in which Kt$^+$ of the compound of Formula (I) is

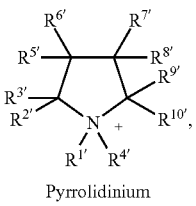

Pyrrolidinium where the substituents R$^{2'}$, R$^{3'}$, R$^{5'}$ to R$^{10'}$ are H and R$^{1'}$ and R$^{4'}$ are each independently of one another straight chain or branched alkyl having 1-20 C atoms.

15. The device of claim 11 comprising the anion difluorodicyanoborate in molar concentrations from 0.1 to 4 M.

16. The device according to claim 11 which is a dye or quantum dot-sensitized solar cell.

17. The device according to claim 11 which is a dye-sensitized solar cell.

18. The device according to claim 17 further comprising a semiconductor and a counter electrode.

19. The device of claim 11, wherein R$^{1'}$ and R$^{4'}$ are each, independently of one another, selected from the group consisting of C$_1$-C$_6$-alkyl, methyl, ethyl, isopropyl, propyl, butyl, sec-butyl, tert-butyl, n-pentyl and n-hexyl.

20. The device of claim 11, wherein the two substituents R$^{1'}$ and R$^{4'}$ are different.

21. The device of claim 11, wherein the two substituents R$^{1'}$ and R$^{4'}$ are the same.

22. The device of claim 11, wherein $R^{2'}$, $R^{3'}$ and $R^{5'}$ to $R^{10'}$ are, independently of one another, selected from the group consisting of H, $C_1$-$C_4$-alkyl, methyl, ethyl, isopropyl, propyl, butyl, sec-butyl and tert-butyl.

23. The device of claim 11, wherein the substituents $R^{2'}$, $R^{3'}$ and $R^{5'}$ to $R^{10'}$ are the same.

24. The device of claim 11, wherein the substituents $R^{2'}$, $R^{3'}$ and $R^{5'}$ to $R^{10'}$ are different.

25. The device of claim 11, wherein two or more of the substituents $R^{2'}$, $R^{3'}$ and $R^{5'}$ to $R^{10'}$ are the same or different.

26. The device of claim 11, wherein $Kt^+$ is defined as

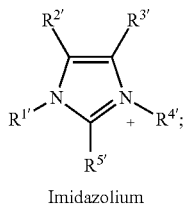

Imidazolium $R^{2'}$ and $R^{3'}$ are H;

$R^{5'}$ is H or straight-chain or branched alkyl having 1 to 4 C atoms; and $R^{1'}$ and $R^{4'}$ are each independently upon each occurrence a straight chain or branched alkyl having 1-20 C atoms, or a straight-chain or branched alkenyl having 3 C atoms.

27. The device of claim 26, wherein $Kt^+$ is 1,3-dialkylimidazolium, 1-alkenyl-3-alkylimidazolium or 1-alkoxyalkyl-3-alkylimidazolium.

28. The device of claim 27, wherein 1,3-dialkylimidazolium is selected from the group consisting of 1-ethyl-3-methylimidazolium, 1-methyl-3-propylimidazolium, 1,2,3-trimethylimidazolium, 1-ethyl-2,3-dimethylimidazolium, 1-propyl-2,3-dimethylimidazolium, 1-butyl-2,3-dimethylimidazolium, 1-butyl-3-methyl-imidazolium, 1-methyl-3-pentylimidazolium, 1-ethyl-3-propylimidazolium, 1-butyl-3-ethylimidazolium, 1-ethyl-3-pentylimidazolium, 1-butyl-3-propyl-imidazolium, 1,3-dimethylimidazolium, 1,3-diethylimidazolium, 1,3-dipropylimidazolium, 1,3-dibutylimidazolium, 1,3-dipentylimidazolium, 1,3-dihexylimidazolium, 1,3-diheptylimidazolium, 1,3-dioctylimidazolium, 1,3-dinonylimidazolium, 1,3-didecylimidazolium, 1-hexyl-3-methylimidazolium, 1-heptyl-3-methylimidazolium, 1-methyl-3-octylimidazolium, 1-methyl-3-nonylimidazolium, 1-decyl-3-methylimidazolium, 1-ethyl-3-hexylimidazolium, 1-ethyl-3-heptylimidazolium, 1-ethyl-3-octylimidazolium, 1-ethyl-3-nonylimidazolium or 1-decyl-3-ethylimidazolium.

29. The device of claim 27, wherein 1-alkoxyalkyl-3-alkylimidazolium is selected from the group consisting of 1-methoxymethyl-3-methylimidazolium, 1-methoxymethyl-3-ethylimidazolium, 1-methoxymethyl-3-butylimidazolium, 1-(2-methoxyethyl)-3-methylimidazolium, 1-(2-methoxyethyl)-3-ethylimidazolium, 1-(2-methoxyethyl)-3-propylimidazolium, 1-(2-methoxyethyl)-3-butylimidazolium, 1-(2-ethoxyethyl)-3-methylimidazolium, and 1-ethoxymethyl-3-methyl-imidazolium.

30. The device of claim 27, wherein 1-alkenyl-3-alkylimidazolium is selected from the group consisting of 1-allyl-3-methyl-imidazolium and 1-allyl-2,3-dimethylimidazolium.

31. The device of claim 26, wherein:

$R^{5'}$ is selected from the group consisting of H, methyl, ethyl, isopropyl, propyl and n-butyl.

32. The device of claim 26, wherein:

a) $R^{1'}$ and $R^{4'}$ are alkyl, wherein $R^{1'}$ and $R^{4'}$ can be the same or different upon each occurrence; and $R^{2'}$, $R^{3'}$ and $R^{5'}$ are hydrogen;

b) $R^{1'}$, $R^{5'}$ and $R^{4'}$ are alkyl, wherein $R^{1'}$, $R^{5'}$ and $R^{4'}$ can be the same or different upon each occurrence; and $R^{3'}$ and $R^{2'}$ are hydrogen;

c) $R^{1'}$ and $R^{4'}$ are $C_1$-$C_{10}$-alkyl, wherein $R^{1'}$ and $R^{4'}$ can be the same or different upon each occurrence; and $R^{2'}$, $R^{3'}$ and $R^{5'}$ are hydrogen;

d) $R^{1'}$, $R^{5'}$ and $R^{4'}$ are $C_1$-$C_{10}$-alkyl, wherein $R^{1'}$, $R^{5'}$ and $R^{4'}$ can be the same or different upon each occurrence; and $R^{3'}$ and $R^{2'}$ are hydrogen;

e) $R^{1'}$, $R^{5'}$ and $R^{4'}$ are $C_1$-$C_3$-alkyl, wherein $R^{1'}$, $R^{5'}$ and $R^{4'}$ can be the same or different upon each occurrence; and $R^{3'}$ and $R^{2'}$ are hydrogen;

f) $R^{1'}$ and $R^{4'}$ are $C_1$-$C_{10}$-alkyl, wherein $R^{1'}$ and $R^{4'}$ can be the same or different upon each occurrence; $R^{5'}$ is H or $C_1$-$C_{10}$-alkyl or $C_1$-$C_{10}$-alkoxy-$C_1$-$C_{10}$-alkyl; and $R^{3'}$ and $R^{2'}$ are hydrogen;

g) $R^{1'}$ and $R^{4'}$ are $C_1$-$C_3$-alkyl, wherein $R^{1'}$ and $R^{4'}$ can be the same or different upon each occurrence; $R^{5'}$ is H or $C_1$-$C_3$-alkyl; and $R^{3'}$ and $R^{2'}$ are hydrogen;

h) $R^{1'}$ is alkyl; $R^{4'}$ is alkoxyalkyl; and $R^{2'}$, $R^{3'}$ and $R^{5'}$ are hydrogen;

i) $R^{1'}$ is alkyl; $R^{4'}$ is alkoxyalkyl; $R^{5'}$ is H or alkyl; and $R^{3'}$ and $R^{2'}$ are hydrogen;

j) $R^{1'}$ is $C_1$-$C_{10}$-alkyl; $R^{4'}$ is $C_1$-$C_{10}$-alkoxy-$C_1$-$C_{10}$-alkyl; $R^{5'}$ is H or $C_1$-$C_{10}$-alkyl; and $R^{3'}$ and $R^{2'}$ are hydrogen;

k) $R^{1'}$ is $C_1$-$C_{10}$-alkyl; $R^{4'}$ is $C_1$-$C_{10}$-alkoxy-$C_1$-$C_{10}$-alkyl; $R^{5'}$ is H or $C_1$-$C_{10}$-alkyl; and $R^{3'}$ and $R^{2'}$ are hydrogen; or l) $R^{1'}$ is $C_1$-$C_4$-alkyl or $C_1$-$C_2$-alkyl; $R^{4'}$ is $C_1$-$C_3$-alkoxy-$C_1$-$C_3$-alkyl; $R^{5'}$ is H or $C_1$-$C_3$-alkyl; and $R^{3'}$ and $R^{2'}$ are hydrogen.

33. The device of claim 26, wherein:

$R^{1'}$ is selected from the group consisting of alkyl, $C_1$-$C_{10}$-alkyl, $C_1$-$C_4$-alkyl, methyl, ethyl, propyl, butyl, pentyl, hexyl, heptyl, octyl, nonyl and decyl;

$R^{4'}$ is selected from the group consisting of alkyl, $C_1$-$C_{10}$-alkyl, $C_1$-$C_{10}$-alkoxy-$C_1$-$C_{10}$-alkyl, $C_1$-$C_3$-alkoxy-$C_1$-$C_3$-alkyl, methyl, ethyl, propyl, butyl, pentyl, hexyl, heptyl, octyl, nonyl, decyl, methoxymethyl, methoxyethyl, ethoxyethyl, and ethoxymethyl;

$R^{5'}$ is hydrogen, methyl, ethyl, isopropyl, propyl or n-butyl or methoxymethyl, methoxyethyl, ethoxyethyl, and ethoxymethyl; and $R^{3'}$ and $R^{2'}$ are hydrogen;

wherein each substituent is independently selected upon each occurrence.

34. The device of claim 26, wherein $R^{1'}$ is selected from the group consisting of methyl, ethyl, propyl, butyl, pentyl, hexyl, heptyl, octyl, nonyl and decyl;

$R^{4'}$ is selected from the group consisting of methyl, ethyl, propyl, butyl, pentyl, hexyl, heptyl, octyl, nonyl, decyl, methoxymethyl, methoxyethyl, ethoxyethyl, and ethoxymethyl;

$R^{5'}$ is hydrogen, methyl, ethyl, isopropyl, propyl or n-butyl; and $R^{3'}$ and $R^{2'}$ are hydrogen;

wherein each substituent is independently selected upon each occurrence.

35. The device of claim 11, wherein Kt⁺ is defined as

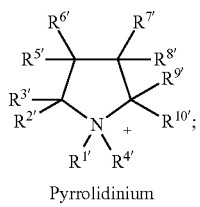

Pyrrolidinium $R^{2'}$, $R^{3'}$, $R^{5'}$ to $R^{10'}$ are H; and
$R^{1'}$ and $R^{4'}$ are each independently of one another (independently selected upon each occurrence) a straight chain or branched alkyl having 1-20 C atoms.

36. The device of claim 35, wherein:
a) $R^{1'}$ and $R^{4'}$ are alkyl, wherein $R^{1'}$ and $R^{4'}$ can be the same or different upon each occurrence; and $R^{2'}$, $R^{3'}$ and $R^{5'}$ to $R^{10'}$ are hydrogen;
b) $R^{1'}$ and $R^{4'}$ are $C_1$-$C_{10}$-alkyl, wherein $R^{1'}$ and $R^{4'}$ can be the same or different upon each occurrence; and $R^{2'}$, $R^{3'}$ and $R^{5'}$ to $R^{10'}$ are hydrogen;
c) $R^{1'}$ is alkyl; $R^{4'}$ is alkoxyalkyl; and $R^{2'}$, $R^{3'}$ and $R^{5'}$ to $R^{10'}$ are hydrogen;
d) $R^{1'}$ is $C_1$-$C_{10}$-alkyl; $R^{4'}$ is $C_1$-$C_{10}$-alkoxy-$C_1$-$C_{10}$-alkyl; and $R^{2'}$, $R^{3'}$ and $R^{5'}$ to $R^{10'}$ are hydrogen;
e) $R^{1'}$ is $C_1$-$C_4$-alkyl; $R^{4'}$ is $C_1$-$C_3$-alkoxy-$C_1$-$C_3$-alkyl; and $R^{2'}$, $R^{3'}$ and $R^{5'}$ to $R^{10'}$ are hydrogen; or
f) $R^{2'}$, $R^{3'}$, $R^{5'}$ to $R^{10'}$ are H.

37. The device of claim 35, wherein
$R^{1'}$ is selected from the group consisting of alkyl, $C_1$-$C_{10}$-alkyl, $C_1$-$C_4$-alkyl, methyl, ethyl, propyl, butyl, pentyl, hexyl, heptyl, octyl, nonyl and decyl;
$R^{4'}$ is selected from the group consisting of alkyl, $C_1$-$C_{10}$-alkyl, $C_1$-$C_{10}$-alkoxy-$C_1$-$C_{10}$-alkyl, $C_1$-$C_3$-alkoxy-$C_1$-$C_3$-alkyl, methyl, ethyl, propyl, butyl, pentyl, hexyl, heptyl, octyl, nonyl, decyl, methoxymethyl, methoxyethyl, ethoxyethyl, and ethoxymethyl; and
$R^{2'}$, $R^{3'}$ and $R^{5'}$ to $R^{10'}$ are hydrogen; and
wherein $R^{1'}$ and $R^{4'}$ are independently selected upon each occurrence.

38. The device of claim 35, wherein:
$R^{1'}$ is selected from the group consisting of methyl, ethyl, propyl, butyl, pentyl, hexyl, heptyl, octyl, nonyl and decyl;
$R^{4'}$ is selected from the group consisting of methyl, ethyl, propyl, butyl, pentyl, hexyl, heptyl, octyl, nonyl, decyl, methoxymethyl, methoxyethyl, ethoxyethyl, and ethoxymethyl; and
$R^{2'}$, $R^{3'}$ and $R^{5'}$ to $R^{10'}$ are hydrogen; and
wherein $R^{1'}$ and $R^{4'}$ are independently selected upon each occurrence.

39. The device of claim 35, wherein Kt+ is selected from the group consisting of 1,1-dialkylpyrrolidinium and 1-alkyl-1-alkoxyalkyl-pyrrolidinium.

40. The device of claim 39, wherein 1,1-dialkylpyrrolidinium is selected from the group consisting of 1,1-dimethylpyrrolidinium, 1-methyl-1-ethylpyrrolidinium, 1-methyl-1-propylpyrrolidinium, 1-methyl-1-butylpyrrolidinium, 1-methyl-1-pentylpyrrolidinium, 1-methyl-1-hexylpyrrolidinium, 1-methyl-1-heptylpyrrolidinium, 1-methyl-1-octylpyrrolidinium, 1-methyl-1-nonylpyrrolidinium, 1-methyl-1-decylpyrrolidinium, 1,1-diethylpyrrolidinium, 1-ethyl-1-propylpyrrolidinium, 1-ethyl-1-butylpyrrolidinium, 1-ethyl-1-pentylpyrrolidinium, 1-ethyl-1-hexylpyrrolidinium, 1-ethyl-1-heptylpyrrolidinium, 1-ethyl-1-octylpyrrolidinium, 1-ethyl-1-nonylpyrrolidinium, 1-ethyl-1-decylpyrrolidinium, 1,1-dipropylpyrrolidinium, 1-propyl-1-methylpyrrolidinium, 1-propyl-1-butylpyrrolidinium, 1-propyl-1-pentylpyrrolidinium, 1-propyl-1-hexylpyrrolidinium, 1-propyl-1-heptylpyrrolidinium, 1-propyl-1-octylpyrrolidinium, 1-propyl-1-nonylpyrrolidinium, 1-propyl-1-decylpyrrolidinium, 1,1-dibutylpyrrolidinium, 1-butyl-1-pentylpyrrolidinium, 1-butyl-1-hexylpyrrolidinium, 1-butyl-1-heptylpyrrolidinium, 1-butyl-1-octyl-pyrrolidinium, 1-butyl-1-nonylpyrrolidinium, 1-butyl-1-decylpyrrolidinium, 1,1-dipentylpyrrolidinium, 1-pentyl-1-hexylpyrrolidinium, 1-pentyl-1-heptyl-pyrrolidinium, 1-pentyl-1-octylpyrrolidinium, 1-pentyl-1-nonylpyrrolidinium, 1-pentyl-1-decylpyrrolidinium, 1,1-dihexylpyrrolidinium, 1-hexyl-1-heptyl-pyrrolidinium, 1-hexyl-1-octylpyrrolidinium, 1-hexyl-1-nonylpyrrolidinium, 1-hexyl-1-decylpyrrolidinium, 1,1-dihexylpyrrolidinium, 1-hexyl-1-heptyl-pyrrolidinium, 1-hexyl-1-octylpyrrolidinium, 1-hexyl-1-nonylpyrrolidinium, 1-hexyl-1-decylpyrrolidinium, 1,1-diheptylpyrrolidinium, 1-heptyl-1-octyl-pyrrolidinium, 1-heptyl-1-nonylpyrrolidinium, 1-heptyl-1-decylpyrrolidinium, 1,1-dioctylpyrrolidinium, 1-octyl-1-nonylpyrrolidinium, 1-octyl-1-decyl-pyrrolidinium, 1,1-dinonylpyrrolidinium, 1-nonyl-1-decylpyrrolidinium or 1,1-didecylpyrrolidinium.

41. The device of claim 39, wherein 1-alkyl-1-alkoxyalkyl-pyrrolidinium is selected from the group consisting of 1-methoxymethyl-1-methyl-pyrrolidinium, 1-methoxymethyl-1-ethyl-pyrrolidinium, 1-(2-methoxyethyl)-1-methylpyrrolidinium, 1-(2-methoxyethyl)-1-ethylpyrrolidinium, 1-(2-methoxyethyl)-1-propylpyrrolidinium, 1-(2-methoxyethyl)-1-butylpyrrolidinium, 1-(2-ethoxyethyl)-1-methylpyrrolidinium, 1-ethoxymethyl-1-ethyl-pyrrolidinium, 1-ethoxymethyl-1-methylpyrrolidinium.

42. The of claim 11, wherein:
a) the electrolyte formulation is a binary system comprising a compound of Formula (I) and a further salt;
b) the electrolyte formulation comprises one or more compounds of Formula (I), iodine and one or more iodide salts;
c) the electrolyte formulation comprises one or more compounds of Formula (I), iodine and two iodide salts;
d) the electrolyte formulation is a ternary system comprising a compound of Formula (I) and two further salts;
e) the electrolyte formulation comprises one or more guanidinium salts and/or
f) the substituents $R^{2'}$, $R^{3'}$ and $R^{5'}$ to $R^{10'}$ are different.

43. The device of claim 11 comprising less than 50% wt, less than 40% wt, less than 30% wt, less than 20% wt, less than 10% wt, less than 5% wt, or less than 1% wt of organic solvent or the electrolyte formulation excludes an organic solvent.

44. The device of claim 11, wherein the electrolyte formulation comprises one or more compounds of the Formula (I) and one or more constituents selected from the group consisting of: one or more further salts, one or more solvents, iodine, one or more iodide salts, one or more compounds containing a nitrogen atom having non-shared electron pairs, one or more redox active species, one or more polymers, one or more metal oxide nanoparticles, one or more dyes, guanidinium thiocyanate and a combination thereof.

45. The device of claim 11, wherein difluorodicyanoborate anion is present in the electrolyte formulation at a concentration ranging from 0.1 to 4 M or 0.8 to 3.5 M.

46. The device of claim 11, wherein the difluorodicyanoborate anion in the electrolyte formulation is present in molar excess over the organic cation Kt⁺ of the compound of Formula (I).

47. The device of claim 11 comprising one or more compounds of the Formula (I), one or more redox couples, optionally one or more further salts, and optionally one or more constituents.

48. The device of claim 47, wherein one or more further salts and one or more constituents are present, and wherein the formulation further comprises one or more components selected from the group consisting of guanidinium thiocyanate, one or more compounds containing a nitrogen atom having non-shared electron pairs, and n-butylbenzimidazole.

49. The device of claim 47 comprising one or more one or more compounds of the Formula (I), iodine, one or more iodide salts, guanidinium thiocyanate, and n-butylbenzimidazole.

50. The device of claim 47, wherein the one or more redox couples is one or more iodide salts comprising an organic cation that is:

a) the same as the cation Kt$^+$ of at least one compound of Formula (I) in the electrolyte formulation;

b) selected from Kt$^+$ as defined herein for at least one compound of Formula (I) in the electrolyte formulation;

c) an imidazolium cation of Formula (IV)

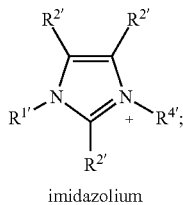

imidazolium d) an imidazolium cation of Formula (IV), wherein: 1) $R^{1'}$ is alkyl, allyl or alkenyl; $R^{4'}$ is alkyl, allyl or alkenyl; and $R^{2'}$ is hydrogen or alkyl; or 2) $R^{1'}$ is alkyl, allyl or alkenyl; $R^{4'}$ is alkyl; and $R^{2'}$ is hydrogen; or 3) $R^{1'}$ is $C_1$-$C_6$-alkyl or allyl; $R^{4'}$ is $C_1$-$C_2$-alkyl; and $R^{2'}$ is hydrogen; or 4) $R^{1'}$ is methyl, ethyl, propyl, butyl, pentyl, hexyl, or allyl; $R^{4'}$ is methyl; and $R^{2'}$ is hydrogen; or e) a pyrrolidinium cation of Formula (V)

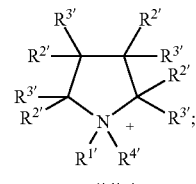

pyrrolidinium or f) a pyrrolidinium cation of Formula (V), wherein: 1) $R^{1'}$ is alkyl, allyl or alkenyl; $R^{4'}$ is alkyl, allyl or alkenyl; and $R^{2'}$ and $R^{3'}$ are hydrogen or alkyl; or 2) $R^{1'}$ is alkyl; $R^{4'}$ is alkyl; and $R^{2'}$ and $R^{3'}$ are hydrogen; or 3) $R^{1'}$ is methyl, ethyl, propyl or butyl; $R^{4'}$ is methyl; and $R^{2'}$ and $R^{3'}$ are hydrogen.

51. The device of claim 50, wherein at least one iodide salt is selected from the group consisting of 1-ethyl-3-methylimidazolium iodide (emim I), 1-propyl-3-methylimidazolium iodide (pmim I), 1-butyl-3-methyl-imidazolium iodide (bmim I), 1-hexyl-3-methylimidazolium iodide (hmim I), 1,3-dimethyl-imidazolium iodide (mmim I), 1-allyl-3-methylimidazolium iodide (amim I), N-butyl-N-methyl-pyrrolidinium iodide (bmpl I) and N,N-dimethyl-pyrrolidinium iodide (mmpl I).

52. The device of claim 11, wherein one or more compounds of the Formula (I) is an ionic liquid.

* * * * *